(12) United States Patent
Seth et al.

(10) Patent No.: US 8,030,071 B2
(45) Date of Patent: Oct. 4, 2011

(54) RESTORATION OF CHOLESTEROL INDEPENDENCE AND ITS USE AS A SELECTABLE MARKER IN NS0 CELL CULTURE

(76) Inventors: Gargi Seth, St. Paul, MN (US);
Wei-Shou Hu, Falcon Heights, MN (US)

( * ) Notice: Subject to any disclaimer, the term of this patent is extended or adjusted under 35 U.S.C. 154(b) by 815 days.

(21) Appl. No.: 11/908,006

(22) PCT Filed: Mar. 10, 2006

(86) PCT No.: PCT/US2006/009030
§ 371 (c)(1),
(2), (4) Date: Sep. 7, 2007

(87) PCT Pub. No.: WO2006/099369
PCT Pub. Date: Sep. 21, 2006

(65) Prior Publication Data
US 2008/0261274 A1    Oct. 23, 2008

Related U.S. Application Data

(60) Provisional application No. 60/660,602, filed on Mar. 11, 2005.

(51) Int. Cl.
*C12N 5/079* (2010.01)
*C12N 5/10* (2006.01)
(52) U.S. Cl. ............ 435/354; 435/375; 435/6; 435/69.1
(58) Field of Classification Search ........................ None
See application file for complete search history.

*Primary Examiner* — James S Ketter

(57) ABSTRACT

Gene complementation is used to restore cholesterol independence in NS lineage murine myeloma cells, such as NS0 and NS 1, yielding a selectable system for recombinant production of polynucleotides and polypeptides.

2 Claims, 6 Drawing Sheets

SEQUENCE LISTING

```
<160> NUMBER OF SEQ ID NOS: 43

<210> SEQ ID NO 1
<211> LENGTH: 320
<212> TYPE: DNA
<213> ORGANISM: Mus musculus

<400> SEQUENCE: 1
tgaaacctcc agctctgccg cccgcttgct tcactcagaa caaagccccc gccgcagact      60
gggggcggcg actgcctgga ttggctatag gacccttgtg tcacgtggct ccgcccctcg     120
gcctatctca cctcacccgg tctgggcgtg gagagaagat gccgagtcgc gattggcggg     180
cctaacgcgc ggaccggatg acgcaggaga ggtggagccg ggccgagcct tgattggtcg     240
aggtgcgcgt ggtcacggat caaggttcag gctaagagaa ccccggtgca gttctacttc     300
ggtgcagggc gtggaagatg                                                 320

<210> SEQ ID NO 2
<211> LENGTH: 18
<212> TYPE: DNA
<213> ORGANISM: Mus musculus

<400> SEQUENCE: 2
gccgtcattc cagccaag                                                    18

<210> SEQ ID NO 3
<211> LENGTH: 18
<212> TYPE: DNA
<213> ORGANISM: Mus musculus

<400> SEQUENCE: 3
cgttgtagcc gcctatgc                                                    18

<210> SEQ ID NO 4
<211> LENGTH: 18
<212> TYPE: DNA
<213> ORGANISM: Mus musculus

<400> SEQUENCE: 4
```

-continued

```
ggtctccgtc agcaggtg                                                 18

<210> SEQ ID NO 5
<211> LENGTH: 20
<212> TYPE: DNA
<213> ORGANISM: Mus musculus

<400> SEQUENCE: 5
gcattgtcca caccagaagg                                               20

<210> SEQ ID NO 6
<211> LENGTH: 20
<212> TYPE: DNA
<213> ORGANISM: Mus musculus

<400> SEQUENCE: 6
aagattgtgg aaggcgtgtc                                               20

<210> SEQ ID NO 7
<211> LENGTH: 22
<212> TYPE: DNA
<213> ORGANISM: Mus musculus

<400> SEQUENCE: 7
cactactcgg actgtctgta tc                                            22

<210> SEQ ID NO 8
<211> LENGTH: 22
<212> TYPE: DNA
<213> ORGANISM: Mus musculus

<400> SEQUENCE: 8
tcagtgtacc atgattgcct tg                                            22

<210> SEQ ID NO 9
<211> LENGTH: 19
<212> TYPE: DNA
<213> ORGANISM: Mus musculus

<400> SEQUENCE: 9
gaacctgctc tgcctgttg                                                19

<210> SEQ ID NO 10
<211> LENGTH: 19
<212> TYPE: DNA
<213> ORGANISM: Mus musculus

<400> SEQUENCE: 10
tcatcgtgga accgtcagc                                                19

<210> SEQ ID NO 11
<211> LENGTH: 22
<212> TYPE: DNA
<213> ORGANISM: Mus musculus

<400> SEQUENCE: 11
tgcctgtgaa agtttgcttc tc                                            22

<210> SEQ ID NO 12
<211> LENGTH: 21
<212> TYPE: DNA
<213> ORGANISM: Mus musculus

<400> SEQUENCE: 12
```

```
aaggatggag ttcgtcaagt g                                           21
```

```
<210> SEQ ID NO 13
<211> LENGTH: 18
<212> TYPE: DNA
<213> ORGANISM: Mus musculus

<400> SEQUENCE: 13
gctgctgctg agtgagtc                                               18

<210> SEQ ID NO 14
<211> LENGTH: 19
<212> TYPE: DNA
<213> ORGANISM: Mus musculus

<400> SEQUENCE: 14
ccttcctacc gagcacctg                                              19

<210> SEQ ID NO 15
<211> LENGTH: 22
<212> TYPE: DNA
<213> ORGANISM: Mus musculus

<400> SEQUENCE: 15
cacacttctt cattcagcca ac                                          22

<210> SEQ ID NO 16
<211> LENGTH: 20
<212> TYPE: DNA
<213> ORGANISM: Mus musculus

<400> SEQUENCE: 16
ggactgccct gaactatgtg                                             20

<210> SEQ ID NO 17
<211> LENGTH: 18
<212> TYPE: DNA
<213> ORGANISM: Mus musculus

<400> SEQUENCE: 17
aggacagcca gccagaac                                               18

<210> SEQ ID NO 18
<211> LENGTH: 20
<212> TYPE: DNA
<213> ORGANISM: Mus musculus

<400> SEQUENCE: 18
aggtgacagg aggcaacttg                                             20

<210> SEQ ID NO 19
<211> LENGTH: 19
<212> TYPE: DNA
<213> ORGANISM: Mus musculus

<400> SEQUENCE: 19
ggcgagacgg aacaggtag                                              19

<210> SEQ ID NO 20
<211> LENGTH: 21
<212> TYPE: DNA
<213> ORGANISM: Mus musculus

<400> SEQUENCE: 20
```
agttgctgta tgtgggtgat g             21

<210> SEQ ID NO 21
<211> LENGTH: 19
<212> TYPE: DNA
<213> ORGANISM: Mus musculus

<400> SEQUENCE: 21
gcaggctgta ggtgaatgg              19

<210> SEQ ID NO 22
<211> LENGTH: 20
<212> TYPE: DNA
<213> ORGANISM: Mus musculus

<400> SEQUENCE: 22
agaatacgca catcccttgg             20

<210> SEQ ID NO 23
<211> LENGTH: 20
<212> TYPE: DNA
<213> ORGANISM: Mus musculus

<400> SEQUENCE: 23
gcgggttgag aggaatatca             20

<210> SEQ ID NO 24
<211> LENGTH: 20
<212> TYPE: DNA
<213> ORGANISM: Mus musculus

<400> SEQUENCE: 24
gatgccaacg accctaagaa             20

<210> SEQ ID NO 25
<211> LENGTH: 20
<212> TYPE: DNA
<213> ORGANISM: Mus musculus

<400> SEQUENCE: 25
aaccacattc tccacgaagg             20

<210> SEQ ID NO 26
<211> LENGTH: 20
<212> TYPE: DNA
<213> ORGANISM: Mus musculus

<400> SEQUENCE: 26
tggcagaaga cgatgacctc             20

<210> SEQ ID NO 27
<211> LENGTH: 20
<212> TYPE: DNA
<213> ORGANISM: Mus musculus

<400> SEQUENCE: 27
ggcaggattc cagcattcag             20

<210> SEQ ID NO 28
<211> LENGTH: 21
<212> TYPE: DNA
<213> ORGANISM: Mus musculus

<400> SEQUENCE: 28

-continued

```
atcttcttcc tcctcgcaca g                                              21

<210> SEQ ID NO 29
<211> LENGTH: 21
<212> TYPE: DNA
<213> ORGANISM: Mus musculus

<400> SEQUENCE: 29
cctcaggttc ctagcagtag c                                              21

<210> SEQ ID NO 30
<211> LENGTH: 22
<212> TYPE: DNA
<213> ORGANISM: Mus musculus

<400> SEQUENCE: 30
gagacactac taccaccgac ac                                             22

<210> SEQ ID NO 31
<211> LENGTH: 19
<212> TYPE: DNA
<213> ORGANISM: Mus musculus

<400> SEQUENCE: 31
caccatccag ccgaagagg                                                 19

<210> SEQ ID NO 32
<211> LENGTH: 22
<212> TYPE: DNA
<213> ORGANISM: Mus musculus

<400> SEQUENCE: 32
caagtgacag acacaaccat tg                                             22

<210> SEQ ID NO 33
<211> LENGTH: 22
<212> TYPE: DNA
<213> ORGANISM: Mus musculus

<400> SEQUENCE: 33
ggctggatat acatacggag tg                                             22

<210> SEQ ID NO 34
<211> LENGTH: 21
<212> TYPE: DNA
<213> ORGANISM: Mus musculus

<400> SEQUENCE: 34
tccaagaagg tgccattact c                                              21

<210> SEQ ID NO 35
<211> LENGTH: 22
<212> TYPE: DNA
<213> ORGANISM: Mus musculus

<400> SEQUENCE: 35
aggataagag gtaagcgttc ac                                             22

<210> SEQ ID NO 36
<211> LENGTH: 21
<212> TYPE: DNA
<213> ORGANISM: Mus musculus

<400> SEQUENCE: 36
```

-continued agcactgtcc tctgaagaac c                                            21

<210> SEQ ID NO 37
<211> LENGTH: 18
<212> TYPE: DNA
<213> ORGANISM: Mus musculus

<400> SEQUENCE: 37
gacggctggc tcggaatc                                                18

<210> SEQ ID NO 38
<211> LENGTH: 20
<212> TYPE: DNA
<213> ORGANISM: Mus musculus

<400> SEQUENCE: 38
tgtccacctt ccagcagatg                                              20

<210> SEQ ID NO 39
<211> LENGTH: 21
<212> TYPE: DNA
<213> ORGANISM: Mus musculus

<400> SEQUENCE: 39
gctcagtaac agtccgccta g                                            21

<210> SEQ ID NO 40
<211> LENGTH: 25
<212> TYPE: DNA
<213> ORGANISM: Mus musculus

<400> SEQUENCE: 40
taggattttt gtgttatgtg gtttt                                        25

<210> SEQ ID NO 41
<211> LENGTH: 25
<212> TYPE: DNA
<213> ORGANISM: Mus musculus

<400> SEQUENCE: 41
ctcttaacct aaaccttaat ccata                                        25

<210> SEQ ID NO 42
<211> LENGTH: 22
<212> TYPE: DNA
<213> ORGANISM: Mus musculus

<400> SEQUENCE: 42
gatttttgtg ttacgtggtt tc                                           22

<210> SEQ ID NO 43
<211> LENGTH: 25
<212> TYPE: DNA
<213> ORGANISM: Mus musculus

<400> SEQUENCE: 43
ctcttaacct aaaccttaat ccgta                                        25

RESTORATION OF CHOLESTEROL INDEPENDENCE AND ITS USE AS A SELECTABLE MARKER IN NS0 CELL CULTURE

This application claims the benefit of U.S. Provisional Application Ser. No. 60/660,602, filed Mar. 11, 2005, which is incorporated herein by reference in its entirety.

BACKGROUND

Different platforms have been investigated for the production of recombinant proteins including bacterial, yeast, insect and mammalian cells. The main advantage of mammalian cell expression is that the mammalian cell properly and efficiently recognizes the signals for synthesis, processing and secretion of eukaryotic proteins. A diverse range of biologics produced in mammalian cells has been licensed in recent years for therapeutic, diagnostic and research purposes. These include thrombolytics, cytokines, growth factors, immunoglobulins, plasminogen activators, erythropoietines and vaccines.

NS0 is a mammalian cell line widely used in recombinant genetic engineering. NS0 cells are non-immunoglobulin secreting mouse myeloma cells. These cells were originally derived from immunoglobulin-producing tumor cells (NS1 cells), and hence they are well equipped for producing and secreting proteins. NS1 cells express intracellular light chain, while NS0 cells do not.

NS0 cells can be genetically manipulated to express a gene whose product is of interest and are widely used in the bioprocess industry to produce recombinant proteins. Currently, the Glutamine Synthetase-NS0 (GS-NS0) system is most commonly used for expressing recombinant proteins in NS0 cells. The GS system is based upon the extremely low levels of endogenous glutamine synthetase activity in NS0 cells. Exogenous supply of GS through expression of the gene is therefore used for selecting transfectants in glutamine free medium. NS0 cells are much more commonly used than NS1 cells in the industry for the purpose of producing recombinant polypeptides such as antibodies, although NS1 cells can be used for this purpose as well.

NS1 cells and derivatives, including NS0 cells, are cholesterol auxotrophs (Chen et al., Exp. Cell Res., 163(1): 117-126, 1986; Sato et al., In Vitro Cell Dev Biol 24(12):1223-8, 1988; Sato et al., Mol Biol Med 2(2):121-34, 1984). These cells therefore require cholesterol in the media for successful growth. Cholesterol supply and delivery to cells has been particularly difficult to deal with in the bioprocess industry, raising issues involving solubility, filterability, dispersion, physical stability and container adhesion.

The observed cholesterol dependence of NS1 mouse myeloma cells has advantageously been used as a selection mechanism for hybridoma production. Myoken et al. (In vitro Cellular & Developmental Biology: J. Tissue Culture Assoc., 25(5):477-80, May 1989) reported that hybridoma cells produced by the fusion of an NS1 cell and an antibody-producing cell capable of synthesizing cholesterol could be selected from a mixture of such cells and unfused myeloma parent cells by culturing the cells in a cholesterol-free medium. See also U.S. Pat. No. 5,110,737 (Myoken et al.).

However, for applications involving recombinant protein production, for example, cholesterol auxotrophy remains a significant drawback to the use of NS0 and NS1 cells. A mechanism for creating cholesterol independence in NS0 and/or NS1 cells would greatly enhance their utility in many diverse biological applications.

SUMMARY OF THE INVENTION

The present invention exploits the cholesterol auxotrophy of NS0 cells by linking the restoration of cholesterol independence with successful expression in the cell of a nucleotide sequence encoding a polypeptide or polynucleotide of interest. In this way, successful expression of a nucleotide sequence can be directly inferred from the survival of the transfectant in media lacking cholesterol. No other selection marker is needed to identify transfectants that express the polypeptide or polynucleotide of interest. Moreover, this technology allows NS0 cells to grow in cholesterol free medium.

In one aspect, the invention provides a method for making a selectable NS0 cell that includes contacting an NS lineage cell, such as an NS0 cell, with a first nucleotide sequence operably encoding a polypeptide or polynucleotide of interest, and a second nucleotide sequence operably encoding a complementing polynucleotide, under conditions to yield a selectable NS0 cell that expresses the polypeptide or polynucleotide of interest and the complementing polynucleotide. Expression of the complementing polynucleotide results in cholesterol independence of the selectable NS0 cell, and cholesterol independence is indicative of expression of the polypeptide or polynucleotide of interest in the NS0 cell. Optionally, after contacting the NS0 cell with the first and second nucleotide sequences, the cell is cultured in cholesterol-free media under conditions to cause production of the complementing polynucleotide and the polypeptide or polynucleotide of interest.

The invention further provides an NS lineage cell, such as an NS0 cell, that includes a first nucleotide sequence that operably encodes a polypeptide or polynucleotide of interest; and a second nucleotide sequence that operably encodes a complementing polynucleotide. Expression of the complementing polynucleotide results in cholesterol independence of the selectable NS0 cell, and cholesterol independence is indicative of expression of the polypeptide or polynucleotide of interest in the NS0 cell.

In another aspect, the invention provides a method for making a polypeptide or polynucleotide of interest. The method includes providing a selectable NS lineage cell, such as an NS0 cell, that expresses the polypeptide or polynucleotide of interest and a complementing polynucleotide. Expression of the complementing polynucleotide results in cholesterol independence of the selectable NS0 cell and is indicative of production of the polypeptide or polynucleotide of interest. The selectable cell is cultured in cholesterol-free media under conditions to cause production of the complementing polynucleotide and the polypeptide or polynucleotide of interest. Optionally, the method further includes isolating the polypeptide or polynucleotide of interest.

The polypeptide or polynucleotide of interest is produced inside the cell and optionally secreted or displayed on the cell surface. The methods of the invention optionally include isolating the polypeptide or polynucleotide of interest. In another embodiment, the polypeptide or polynucleotide of interest imparts a selected feature, characteristic or function to the NS0; for example it can include a metabolic enzyme, an anti-apoptotic protein, a cell cycle regulator protein or a regulator protein that affects organelle biogenesis. The polypeptide of interest can include an antibody, for example, or an enzyme.

The complementing polynucleotide encodes a polypeptide selected from the group consisting of a 17β-hydroxysteroid dehydrogenase type 7 (Hsd17b7), biologically active analogs, derivatives and subunits thereof. Alternatively, the complementing polynucleotide encodes a truncated sterol regulatory element binding protein (SREBP) that upregulates production of Hsd17b7, and biologically active analogs, derivatives and subunits thereof, for example SREBP1 and/or SREBP2.

In another aspect, the invention provides a method for making a cholesterol independent NS0 cell that transfecting an NS0 cell with a nucleotide sequence that operably encodes a complementing polypeptide selected from the group consisting of a 17β-hydroxysteroid dehydrogenase type 7 (Hsd17b7), a truncated sterol regulatory element binding protein (SREBP) that upregulates production of Hsd17b7, and biologically active analogs, derivatives and subunits thereof; and culturing the transfected NS0 cell under conditions to cause expression of the complementing polynucleotide.

In yet another aspect the invention provides a method for making a selectable NS lineage cell, for example an NS0 cell, that involves transfecting an NS0 cell with a first nucleotide sequence operably encoding a polypeptide or polynucleotide of interest; and a second nucleotide sequence operably encoding a complementing polynucleotide that encodes a polypeptide selected from the group consisting of a 17β-hydroxysteroid dehydrogenase type 7 (Hsd17b7), a truncated sterol regulatory element binding protein (SREBP) that upregulates production of Hsd17b7, and biologically active analogs, derivatives and subunits thereof; and culturing the transfected NS0 cell under conditions to cause expression of the complementing polynucleotide; wherein expression of the complementing polynucleotide results in cholesterol independence of the selectable NS0 cell, and wherein cholesterol independence is indicative of expression of the polypeptide or polynucleotide of interest in the NS0 cell. In one embodiment, the NS0 cell is transfected with an expression vector that includes the first and second nucleotide sequences; in another embodiment, the NS0 cell is transfected with a first expression vector that contains the first nucleotide sequence and a second expression vector that contains the second nucleotide sequence. A cholesterol independent NS lineage cell, such as an NS0 cell, prepared by the methods of the invention is also included.

In another aspect, the invention provides selectable NS0 cell that includes an expression cassette that includes (a) a first nucleotide sequence encoding a polypeptide or polynucleotide of interest, and (b) a second nucleotide sequence encoding Hsd17b7, wherein the first and second nucleotide sequences are linked such that production of Hsd17b7 protein is indicative of production of the polypeptide or polynucleotide of interest.

In yet an other aspect, the invention provides a selectable NS0 cell that includes an expression cassette that includes (a) a first nucleotide sequence encoding a polypeptide or polynucleotide of interest, and (b) a second nucleotide sequence encoding a truncated SREBP protein, wherein the first and second nucleotide sequences are linked such that production of a truncated SREBP protein is indicative of production of the polypeptide or polynucleotide of interest.

Also provided by the invention is a method for making a selectable mammalian cell. The method includes inhibiting or eliminating expression of an hsd17b7 gene of the cell to yield a cholesterol dependent cell, and contacting the cell with a first nucleotide sequence operably encoding a polypeptide or polynucleotide of interest, and a second nucleotide sequence operably encoding a complementing polynucleotide, under conditions to yield a selectable cell that expresses the polypeptide or polynucleotide of interest and the complementing polynucleotide; wherein expression of the complementing polynucleotide results in cholesterol independence of the selectable cell, and wherein cholesterol independence is indicative of expression of the polypeptide or polynucleotide of interest in the cell. Optionally, after contacting the cell with the first and second nucleotide sequences the cell is cultured in cholesterol-free media under conditions to cause production of the complementing polynucleotide and the polypeptide or polynucleotide of interest The complementing polynucleotide preferably encodes a polypeptide selected from the group consisting of a 17β-hydroxysteroid dehydrogenase type 7 (Hsd17b7), a truncated sterol regulatory element binding protein (SREBP), and biologically active analogs, derivatives and subunits thereof.

Unless otherwise specified, "a," "an," "the," and "at least one" are used interchangeably and mean one or more than one.

DETAILED DESCRIPTION OF ILLUSTRATIVE EMBODIMENTS

Figure 1:
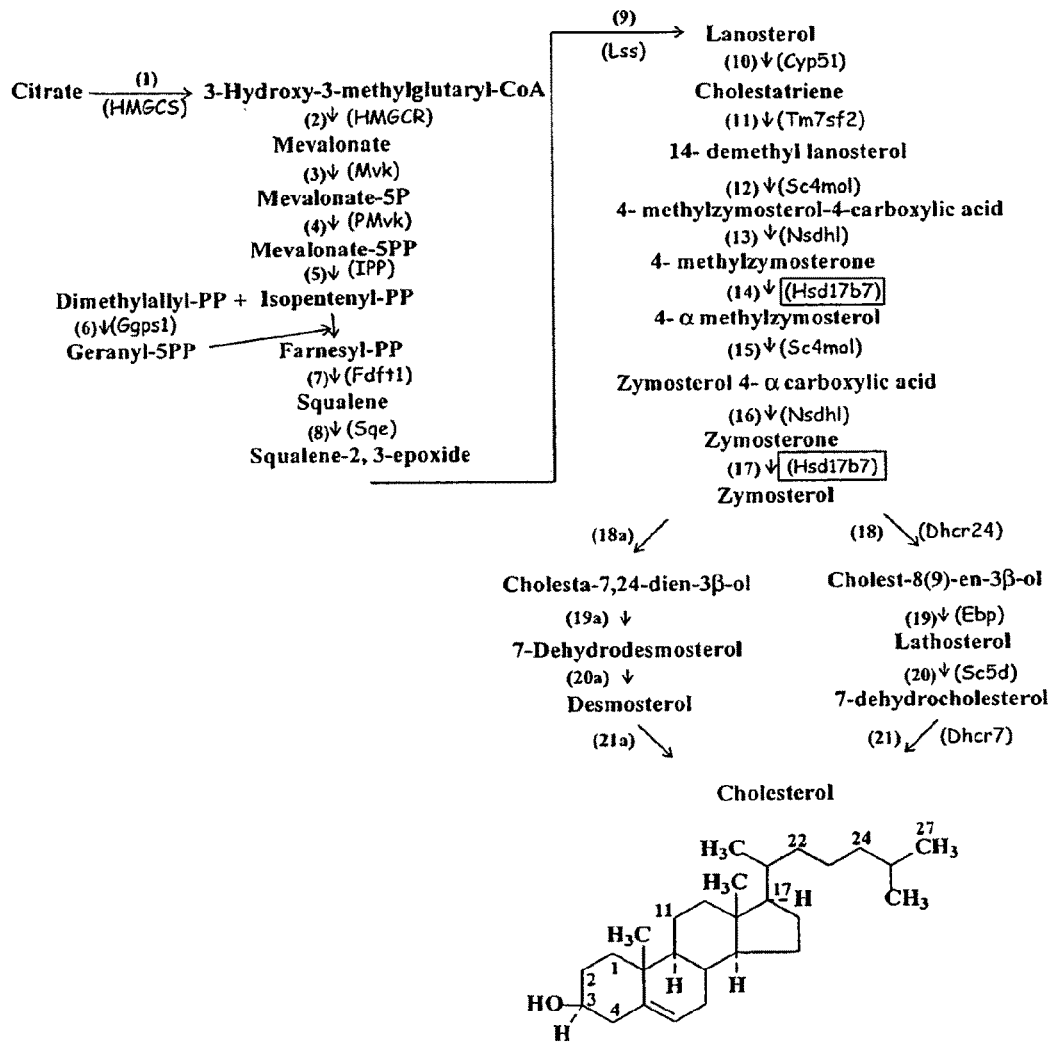
FIG. 1 shows the cholesterol biosynthesis pathway. Abbreviations: Hydroxymethylglutaryl-CoA synthase (HMGCS), Hydroxymethylglutaryl-CoA reductase (HMGCR), Mevalonate kinase (Mvk), Phosphomevalonate kinase (PMvk), Isopentenyl-diphosphate delta-isomerase (IPP), Geranylgeranyl diphosphate synthase 1 (Ggps1), Farnesyldiphosphate farnesyl transferase 1 (Fdft1), Squalene epoxidase (Sqe), Oxidosqualene cyclase (Lss), Lanosterol 14alpha demethylase (Cyp51), Steroid 14 reductase (Tm7sf2), Sterol C4 methyl oxidase-like (Sc4 mol), C3 sterol dehydrogenase (Nsdhl), 3 ketoreductase (Hsd17b7), 24-dehydrocholesterol reductase (Dhcr24), Phenylalkylamine $Ca^{2+}$ antagonist (amopamil) binding protein (Ebp), sterol-C5-desaturase (Sc5d), 7-dehydrocholesterol reductase (Dhcr7).

The present invention provides a genetically modified NS lineage mouse myeloma cell, preferably an NS0 or NS1 cell, that is cholesterol independent, as well as methods for making and using such cells.

Cholesterol independent NS0 and NS1 cells biosynthesize cholesterol and do not need exogenously supplied cholesterol in order to grow. Thus, unlike typical NS0 and NS1 cells such as those commonly used in recombinant technologies, cholesterol-independent NS0 and NS1 cells can grow in a cholesterol-free medium.

In a preferred embodiment, the cholesterol independent NS0 or NS1 cell expresses a polypeptide or polynucleotide of interest, and expression of the polypeptide or polynucleotide of interest is linked to cholesterol independence. In this way, restoration of cholesterol independence can be used as a selectable marker to identify successful transfectants in the absence of cholesterol in the media.

Cholesterol auxotrophs that can be engineered to produce cholesterol according to the invention include, without limitation, any NS1 mouse myeloma cell or its derivative or subclone, including an NS0 cell. NS0 mouse myeloma cells, which represent a particularly preferred cell line for use in the invention, are derivatives of NS1 mouse myeloma cells. Moreover, NS0 exists as a number of distinct subclone lines that are well-known to the art, and those subclone lines are included in the invention. The term "NS0 cell" as used herein is therefore intended to be inclusive of subclones and derivatives of NS0 cells; likewise the term "NS1 cell" as used herein is intended to be inclusive of subclones and derivatives of NS1 cells, including an NS0 cell, unless otherwise noted.

The NS0 and NS1 cells, including derivatives and subclones, that can be engineered according to the invention to produce cholesterol include both wild-type cells and genetically modified cells, without limitation, as well as cell fusions that comprise NS0 or NS1 cells, including transfectomas and hybridomas formed using NS0 or NS1 cells. NS0 cells, for example, have been used for a number of years as fusion partners for the production of hybridoma cells producing monoclonal antibodies, and are now also an important host cell for the engineered production of recombinant polypeptides in their own right. Examples of myeloma cells arising from the NS (Non-Secreting) lineage that are useful in the present invention are described in Barnes et al., Cytotechnology 32:109-123, 2000. NS1 cells, for example (formerly know as 289-16 cells), synthesize the light chain but no heavy chain and hence do not secrete immunoglobulin. NS0 cells represent a subline generated from the NS1 line, and do not secrete or synthesize either immunoglobulin heavy or light chains. It should be noted that recombinant NS0 cells, including those that already possess one or more selectable markers can be used in the present invention. For example, the NS0 cell can be an NS0 cell that has been transfected with a glutamine synthetase (GS) vector to yield a GS-NS0 cell, thereby allowing selection in a glutamine-free medium; GS-NS0 cells contain extremely low levels of endogenous glutamine synthetase activity. Another NS0 cell is one that expresses guanine phosphoribosyl transferase (gpt), wherein selection can be accomplished using mycophenolic acid. Furthermore, while the description of the invention refers predominantly to NS0 cells, it is to be understood that the description is equally applicable to NS1 cells and other derivatives or subclones of NS0 or NS1 cells.

Preferably, cholesterol independence in the NS0 cells of the invention is achieved through gene complementation. The gene complementation strategies used to produce the modified, cholesterol independent NS0 cells of the invention are based on the discovery (see Example I) that cholesterol auxotrophy in NS0 cells results from a deficiency of 17β-hydroxysteroid dehydrogenase type 7 (Hsd17b7). The gene encoding Hsd17b7, hsd17b7, was found to be expressed in NS0 cells, but only at very low levels. The present invention provides for the restoration of cholesterol independence by, for example, transfecting NS0 cells with a polynucleotide that operably encodes a polypeptide having 17β-hydroxysteroid dehydrogenase type 7 activity; and/or by transfecting NS0 cells with a polynucleotide that serves as, or operably encodes, a biomolecule that upregulates expression of Hsd17b7 in the NS0 cell. For example, cholesterol deficiency can be overcome by using gene complementation strategies to cause the cell to express larger quantities of Hsd17b7, or to cause the cell to overexpress certain regulatory proteins, particularly steroid regulatory element binding proteins such as those encoded by srebp1/srebp2 that, in turn, upregulate. hsd17b7. A polynucleotide "operably encodes" a polypeptide if it contains the regulatory elements needed to cause transcription and translation of the encoded polypeptide. Typically the polynucleotide includes, for example, a promoter that is "operably linked" to a nucleic acid sequence in that it does, or can be used to, control or regulate transcription of polynucleotide. The promoter can be a constitutive or an inducible promoter.

In a particularly preferred embodiment of the invention, gene complementation to restore cholesterol independence is coupled with the expression of a nucleotide sequence of interest, termed herein a "selected" nucleotide sequence. The cholesterol auxotrophy of NS0 cells is advantageously exploited by linking restoration of cholesterol independence with successful transfection. In this embodiment, cholesterol independence serves as a selectable marker evidencing successful transfection and expression of the nucleotide sequence of interest.

The selected nucleotide sequence operably encodes any polynucleotide or polypeptide of interest. In one embodiment, the selected nucleotide sequence is one that is already present in the unmodified NS0 cell, in which case the modified NS0 cell is characterized by overexpression of the selected nucleotide sequence compared to unmodified NS0 cells. In another embodiment, the selected nucleotide sequence is foreign to the NS0 cell; i.e., it is not present in an unmodified NS0 cell. Cholesterol independence is achieved by transfecting the NS0 cell with one or more expression vectors that express not only the complementing gene product, but also the polypeptide or polynucleotide of interest. In this way, restoration of cholesterol independence becomes a convenient selectable marker for successful transfection and expression of the polypeptide or polynucleotide of interest.

Expression of a nucleotide sequence of interest can be directly inferred from the survival of the transfectant in media lacking cholesterol. No other selection marker is needed to identify transfectants that express the polypeptide or polynucleotide of interest. Moreover, as noted above, this technology advantageously allows recombinant production of a polypeptide or polynucleotide in NS0 cells cultured or cultivated in cholesterol-free medium.

The invention provides a number of gene complementation strategies for associating the restoration of cholesterol independence with the expression of a nucleotide sequence of interest. These strategies involve the introduction into the NS0 cell of a complementing polynucleotide. In this context, a "complementing polynucleotide" is one that complements the inactive Hsd17b7 gene; for example, it can be a polynucleotide that encodes a polypeptide that supplies a biological activity that directly or indirectly increases the level of Hsd17b7 activity in the NS0 cell.

In a first embodiment, gene complementation is used to directly increase the level of 17β-hydroxysteroid dehydrogenase type 7 (Hsd17b7) activity in the NS0 cell. Hsd17b7 is the missing enzyme that is required for cholesterol biosynthesis in NS0 cells. The complementing polynucleotide sequence that is transfected into the NS0 cells is a polynucleotide sequence operably encoding Hsd17b7, or a biologically active derivative, analog or subunit thereof; for example, the hsd17b7 gene itself. Expression of this polynucleotide sequence causes production of the dehydrogenase activity that is missing from NS0 cells but required for cholesterol biosynthesis.

Optionally, expression of Hsd17b7 is further increased by supplying to the transfectant an Hsd17b7 inhibitor, thereby forcing hsd17b7 to be transcribed at an even higher level as a result of, for example, gene amplification or insertion of the coding sequence into a transcriptionally active site ("hot spot") in the cell's genome. The inhibitor is preferably an analog of a natural substrate of Hsd17b7 that functions as an antagonist. Hsd17b7 takes part in a multi-step demethylation reaction during conversion of lanosterol to lathosterol, functioning as a 3-ketosteroid reductase. It converts 4-methyl zymosterone to 4-methyl zymosterol, and also zymosterone to zymosterol. Inhibitory analogs of one or more of these substrates can be added to the medium to force Hsd17b7 into higher production. This strategy is particularly useful for the production of a recombinant protein product, such as an antibody.

In a second embodiment, the complementing polynucleotide sequence encodes the truncated form of a regulatory protein that upregulates expression of Hsd17b7, for example, one or more sterol regulatory element binding proteins (SREBP), preferably SREBP-1 and/or SREBP-2, or a biologically active derivative, analog or subunit thereof. The gene products of srebp1 and srebp2 are global regulators of fatty acid and cholesterol biosynthesis genes respectively, and are involved in the regulation of hsdb717. This embodiment of the invention thus employs an indirect method of increasing Hsd17b7 activity in an NS0 cell. Normally SREBPs are expressed in the cell and located in the endoplasmic reticulum membrane. When fatty acids or cholesterol are undersupplied, SREBP is truncated in Golgi. After cleavage, the amino terminal functions as a transcription factor and is translocated to the nucleus where it activates expression of cholesterol/fatty acid biosynthesis/metabolism genes. This portion of the protein molecule (i.e., the truncated form or cleavage product, also referred to as the "dominant positive form") binds to the regulatory region of DNA that is under the control of either SREBP1 or SREBP2 and turns on the transcription of those genes, such as hsd17b7 (see, e.g., Horton et al., J. Clin. Invest. 101(11): 2331-9, 1998 (SREBP2); Shimano et al., J. Clin. Invest. 98(7): 1575-84, 1996 (SREBP1a); Horton et al., Proc Natl Acad Sci USA, 100:12027-32, 2003 (list of genes regulated by SREBP)). By expressing the active, truncated, dominant positive form of an SREBP, or a biologically active derivative, analog or subunit thereof, fatty acid synthesis and/or cholesterol synthesis genes remain under an "induced" condition in the genetically modified NS0 cell in this embodiment of the invention, because the feedback inhibition loop that otherwise limits the production of the active, truncated cleavage product is circumvented. Transcription of the fatty acid and cholesterol synthesis genes that are otherwise repressed under normal conditions is thereby "turned on." See, e.g., Shimano et al., J. Clin. Invest. 98(7):1575-1584, 1996; Horton et al, J. Clin. Invest. 101(11):2331-2339, 1998; Horton et al., Proc. Nat'l. Acad. Sci. USA, 100(21): 12027-12032, 2003; Hua et al., Proc. Nat'l. Acad. Sci. USA 90:11603-11607, 1993; and Shimano et al., Prog. Lipid Res 40: 439-452, 2001.

It should be understood that, as used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor do are they intended to imply or distinguish whether the polypeptide is produced using recombinant techniques, chemical or enzymatic synthesis, or is naturally occurring.

Likewise, the term "polynucleotide" refers broadly to a polymer of two or more nucleotides covalently linked in a 5' to 3' orientation. The terms nucleic acid, nucleic acid molecule, and oligonucleotide and polynucleotide included within the definition of polynucleotide and these terms are used interchangeably. It should be understood that these terms do not connote a specific length of a polymer of nucleotides, nor do are they intended to imply or distinguish whether the polynucleotide is produced using recombinant techniques, chemical or enzymatic synthesis, or is naturally occurring.

A "biologically active" analog, subunit or derivative of a polypeptide is a polypeptide that exhibits the same type of activity, such as enzymatic activity or binding activity, or the polypeptide. For example, a biologically active analog, subunit or derivative of Hsd17b7 is a polypeptide that exhibits 17β-hydroxysteroid dehydrogenase type 7 activity. Examples of methods for measuring Hsd17b7 activity can be found in Marijanovic et al., Mol Endocrinol, 17:1715-25, 2003. A biologically active analog, subunit or derivative of an SREBP protein is one that binds to a sterol response element typically located in the vicinity of, or upstream of, the promoter region of a gene, thereby affecting expression of the gene. Binding of SREBP to DNA can be detected by a change in gene expression or by physical methods such as differential scanning calorimetry and the like, in accordance with methods detailed in references cited herein as well as those well known in the art.

A biologically active "subunit" of a polypeptide is one that has been truncated at either the N-terminus, or the C-terminus, or both, by one or more amino acids, as long as the truncated polypeptide retains bioactivity and contains at least 7 amino acids, more preferably at least 10 amino acids, most preferably at least 12 amino acids.

A biologically active "analog" of a polypeptide includes a polypeptide that has been modified by the addition, substitution, or deletion of one or more contiguous or noncontiguous amino acids, or that has been chemically or enzymatically modified, e.g., by attachment of a reporter group, by an N-terminal, C-terminal or other functional group modification or derivatization, or by cyclization, as long as the analog retains biological activity. An analog can thus include additional amino acids at one or both of the termini of a polypeptide.

Substitutes for an amino acid in the polypeptides are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide. For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ee, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Preferred biologically active analogs of Hsd17b7 or SREBP or any of their constituent peptides include those analogs that are at least 80% identical, more preferably 85% identical, more preferably at least 90% identical, even more preferably at least 95% identical, and most preferably at least 96%, 97%, 98% or 99% identical to Hsd17b7 or SREBP or their constituent peptides. Such analogs contain one or more amino acid deletions, insertions, and/or substitutions relative to Hsd17b7 or SREBP, and may further include chemical and/or enzymatic modifications and/or derivatizations as described above.

It should further be understood that the class of nucleotide sequences that encode a selected polypeptide sequence is large but finite, and the nucleotide sequence of each member of the class can be readily determined by one skilled in the art by reference to the standard genetic code, wherein different nucleotide triplets (codons) are known to encode the same amino acid. Likewise, a polynucleotide that encodes a biologically active analog or subunit of Hsd17b7 or SREBP includes the multiple members of the class of polynucleotides that encode the selected polypeptide sequence.

Moreover, a polynucleotide that "encodes" a polypeptide optionally includes both coding and noncoding regions, and it should therefore be understood that, unless expressly stated to the contrary, a polynucleotide that "encodes" a polypeptide is not structurally limited to nucleotide sequences that encode a polypeptide but can include other nucleotide sequences outside (i.e., 5' or 3' to) the coding region.

Polynucleotides can be DNA, RNA, or a combination thereof, and can include any combination of naturally occurring, chemically modified or enzymatically modified nucleotides. Polynucleotides include a vector, such as an expression or cloning vector as described in more detail below. A vector useful in the present invention can be circular or linear, single-stranded or double-stranded, and can include DNA, RNA, or any modification or combination thereof. The vector can be a plasmid, a cosmid, or a viral vector, such as baculovirus. A vector suitable for achieving gene complementation according to the invention is preferably an expression vector that is expressible in mammalian cell culture.

When cholesterol independence is used according to the invention as a selection marker for successful transfection and expression of a selected nucleotide sequence, the selected nucleotide sequence delivered with the complementing polynucleotide can encode any polypeptide or polynucleotide of interest. As noted above, the polypeptide or polynucleotide encoded by the selected nucleotide sequence can be endogenous (naturally occurring) or heterologous (not naturally occurring, also referred to as exogenous or foreign) with respect to NS0.

In one example, the selected nucleotide sequence encodes a polypeptide product, such as an antibody or other polypeptide of interest, which can be isolated from the NS0 cell. Optionally, the polypeptide is secreted by the NS0 cell and isolated from the media. Table 1 of Barnes et al. (Cytotechnology 32:109-123, 2000) shows examples of recombinant proteins that can be expressed using the GS system in NS0 cells, and any of these polypeptides can likewise be expressed in NS0 cells using the method of the present invention. Examples include antibodies for example anti-IL 2 receptor α chain (ZENAPAX, Hoffman La Roche/Protein Design Labs), anti-RSV (SYNAGIS, MedImmune), Anti-CD33 (MYLOTARG, Wyeth) and anti-α4-subunit of α4β1 and α4β7 integrins (TYSABRI, Biogen/Elan), proteases and protease inhibitors, cytokines, hormones and growth factors, cell surface markers and receptors, and intracellular proteins. Indeed, two or more selection systems (e.g., GS and cholesterol independence) can be used together, each to express one or more different polypeptides. The invention thus also provides a method for making a polypeptide (or polynucleotide) of interest. The method involves culturing a cholesterol independent NS0 cell which expresses a polypeptide or polynucleotide of interest, and in which expression of the polypeptide or polynucleotide is linked to cholesterol independence, under conditions and for a time sufficient to allow production of the polypeptide or polynucleotide, followed by isolating the polypeptide or polynucleotide. It should be noted that the terms "culturing" and "cultivating" are used herein interchangeably. The recombinant product can be isolated at the end of the culture period or during a continuous culture.

In another example, the selected nucleotide sequence encodes a polypeptide that remains inside the NS0 cell and imparts a desired feature, characteristic or function to the NS0 cell. In this way, for example, the invention can be used in "cellular engineering" to improve the characteristics of an NS lineage cell that is already being used to produce a polypeptide (e.g., an antibody or other protein) or polynucleotide of interest, for example using the GS-NS0 system. The desired feature, characteristic or function can, for example, enhance the efficiency of the production of another polypeptide product by the NS0 cell. In another example, the selected nucleotide sequence encodes an RNA molecule that imparts a desired feature, characteristic or function to the NS0 cell. For example, the RNA can affect transcription or translation of an NS0 gene, as by functioning as an antisense RNA, double-stranded RNA, siRNA or a ribozyme. An example of a gene endogenous to NS0 that could be targeted, for example with antisense RNA, in accordance with the invention is lactate dehydrogenase (to reduce lactate production). The polypeptide or polynucleotide expressed in the NS0 cell from the selected nucleotide sequence can be selected so as to result in a physiological favorable characteristic ("cellular engineering") such as improved shear resistance, more efficient protein folding and/or glycosylation (e.g., by encoding a chaperonin molecule), better secretion of recombinant protein products, tolerance to osmotic stress and temperature shift, increased robustness in the presence of toxic metabolites, and the like. Cellular engineering can likewise include the introduction of a metabolic enzyme, an anti-apoptotic gene or protein, a cell cycle regulator protein or a regulator protein that affects organelle biogenesis.

Culture conditions for NS0 cells are well-known; see, e.g., Gorfien et al., Biotechnol Prog 16(5):682-7, 2000; Keen et al., Cytotechnology 17(3):203-211, 1995.

The invention provides a method for making a cholesterol independent NS0 cell, wherein cholesterol independence is linked to expression of a selected nucleotide sequence and thereby serves as a selectable marker. This results in a selectable system for transfection and successful production of the recombinant polypeptide or polynucleotide. There are a number of different ways to deliver the complementing polynucleotide and the selected nucleotide sequence to the NS0 cell such that restoration of cholesterol independence functions as a selection marker for successful transfection of the NS0 cell with the selected nucleotide sequence encoding the polypeptide or polynucleotide of interest. The invention is thus not intended to be limited by a particular method of linking restoration of cholesterol independence with transfection of the selected nucleotide sequence encoding the polypeptide or polynucleotide of interest.

In one embodiment of the invention, the NS0 cell is transfected with an expression vector containing an expression cassette that includes (a) a first nucleotide sequence that operably encodes a polypeptide or polynucleotide of interest (i.e., a first coding sequence), and (b) a second nucleotide sequence that operably encodes a complementing polypeptide (e.g., Hsd17b7 and/or an SREBP protein) (i.e., a second coding sequence) which imparts cholesterol independence to the cell. It should be noted that the "first" and "second" sequences can be present in either order. The first nucleotide sequence can be any selected nucleotide sequence, without limitation, that encodes a polypeptide or polynucleotide of interest. The expression cassette further includes one or more regulatory elements, such as a promoter, operably linked to the coding region(s) that facilitate expression of the coding regions. The expression cassette is constructed such that if the complementing polynucleotide is expressed, the polypeptide or polynucleotide of interest is also expressed. It should of course be understood that the vectors and expression cassettes used to transfect NS0 cells in accordance with the invention are also encompassed by the invention, as well as methods for making and using such vectors and expression cassettes.

An expression vector that includes both the first and second coding sequences can, for example, take the form of a dicistronic expression vector, such that the two coding sequences are each under the control of their own promoters, which may be the same or different. Alternatively, the two coding sequences can be under the control of a single promoter, with an internal ribosome entry site (IRES) positioned between the first and second nucleotide sequences. More than two coding sequences can be used, in that the expression of two or more polypeptides or polynucleotides of interest can be linked to expression of the complementing polynucleotide, as in a multi-cistronic vector. When the first coding sequence encodes a polypeptide, the expression vector may encode each polypeptide independently or may encode a single fusion polypeptide, optionally with a cleavage site in between the two coding regions. The coding regions can be present in either order. A promoter can be inducible or constitutive.

In another embodiment of the invention, expression of the polypeptide or polynucleotide of interest is linked to expression of the complementing polynucleotide by co-transfecting the NS0 cell with two or more different expression vectors, and maintaining selection pressure to achieve successful co-transfection. A first expression vector includes a first nucleotide sequence that encodes the polypeptide or polynucleotide of interest (i.e., a first coding sequence), and a second expression vector includes a second nucleotide sequence encoding the complementing polypeptide (e.g., Hsd17b7 and/or an SREBP protein) (i.e., a second coding sequence). Multiple first expression vectors could be used, each capable of expressing a different polynucleotide or polypeptide of interest. The expression vectors further include one or more regulatory elements, such as a promoter, operably linked to the coding region(s) that facilitate expression of the coding regions. Selection pressure is maintained by insuring that the amount of the first expression vector (which carries the nucleotide sequence encoding the polypeptide or polynucleotide of interest) that is supplied to the NS0 cell is well in excess (e.g., about 5× to 10×) the amount of the second expression vector (which carries the polynucleotide for use in gene complementation) that is supplied to the NS0 cell.

By complementing the deficiency responsible for cholesterol auxotrophy, expression of Hsd17b7 restores cholesterol independence to the NS0 cell and therefore serves as a convenient selection marker. Likewise, expression of one or more truncated form of SREBPs increases expression of Hsd17b7 and thus also facilitates cholesterol independence. By indirectly complementing the deficiency responsible for cholesterol auxotrophy through upregulation of endogenous Hsd17b7, expression of the SREBP(s) restores cholesterol independence to the NS0 cell and therefore serves as a convenient selection marker. In each of these embodiments, survival of the cell in cholesterol free media indicates the presence of the complementing polynucleotide and thus also the polypeptide or polynucleotide of interest, thereby identifying a successful transfectant.

In summary, expression of Hsd17b7 and/or truncated SREBP alleviates NS0 cell's requirement to grow in the presence of cholesterol. These genes (hsd17b7 and srebp) can thus be utilized as selectable markers (independently or together) in NS0 cells to identify successful transfectants in the absence of cholesterol in the medium. The present invention allows for selection of cells, in cholesterol-free media, that have taken up the plasmid during transfection and are stably expressing hsd17b7 and/or srebp gene products. When linked directly or indirectly to the expression of a polypeptide or polynucleotide of interest, these complementing gene products form the basis of a powerful selection system in NS0 cells. Moreover, expression of Hsd17b7 and/or SREBP allows NS0 cells to grow in a cholesterol-free medium without need to go through long and tedious adaptation procedures currently being followed in the industry to reach a cholesterol independent phenotype.

It should be noted that another aspect of the invention includes cloning a nucleotide sequence operably encoding Hsd17b7, such as the hsd17b7 gene, into NS0 to correct its cholesterol auxotrophy. The present invention thus also includes an NS0 cell comprising a cloned hsd17b7 sequence that expresses Hsd17b7. This cell can be used with other selection systems, such as the Glutamine Synthetase-NS0 (GS-NS0) system described above for expressing recombinant proteins in NS0 cells. Optionally, one or more SREBP proteins, such as SREBP1 and/or SREBP2, are cloned into NS0 to further restore cholesterol independence.

Additionally, it is envisioned that this selection system can be expanded from NS0 cells to other cell types. Cholesterol auxotrophy could be introduced into other mammalian cells, for example CHO cells, by disrupting, e.g., by silencing, knocking out, knocking down, or mutating, the hsd17b7 gene. Restoration of cholesterol independence using an expression cassette as described above can be used to select successful transfectants.

EXAMPLES

The present invention is illustrated by the following examples. It is to be understood that the particular examples, materials, amounts, and procedures are to be interpreted broadly in accordance with the scope and spirit of the invention as set forth herein.

Example I

17β-Hydroxysteroid Dehydrogenase Type 7 (Hsd17b7) Reverts Cholesterol Auxotrophy In NS0 Cells NS0 is a host cell line widely used for the production of recombinant therapeutic proteins. In this work, we investigated the cholesterol dependent phenotype of NS0 cells. Growth response to different precursors and comparative transcript analyses pointed to deficiency of 17β-hydroxysteroid dehydrogenase type 7 (Hsd17b7) in NS0 cells. Hsd17b7 was previously shown to encode for an enzyme involved in estrogenic steroid biosynthesis. Its recent cloning into a yeast mutant deficient in ERG27 led to its functional characterization as the 3-ketoreductase of the cholesterol biosynthesis pathway. To ascertain that its cholesterol biosynthesis is blocked at the reduction reaction catalyzed by Hsd17b7, we genetically engineered NS0 cells to over express Hsd17b7. The stable transfectants of Hsd17b7 were able to grow independent of cholesterol. The results affirm the role of Hsd17b7 in the cholesterol biosynthesis pathway in mammals. Further, the findings allow for rational engineering of this industrially important cell line to alleviate their cholesterol dependence. See Seth et al., J. Biotechnol. 121:241-252, 2006.

Introduction

NS0 is one of the primary host cell lines used for the production of recombinant therapeutics (Chu et al., Curr Opin Biotechnol, 12:180-7, 2001; Zhou et al., Biotechnology & Bioengineering, 55:783-792, 1997). Human therapeutics produced in NS0 cells include Zenapax™, Remicade™ and Synagis™. It is a murine myeloma cell line that was established from mineral oil induced plasmacytomas in 1960s (Horibata et al., Exp Cell Res, 60:61-77, 1970; Barnes et al., Cytotechnology, 32:109-123, 2000) NS0 cells require an exogenous supply of cholesterol for their survival and growth. Due to its low solubility, cholesterol is often supplied as a conjugate with serum albumin, or as complexes with cyclodextrin (Keen et al., Cytotechnol, 17:203-211, 1995; Ohmori, J Immunol Methods, 112:227-33, 1988). In pursuing chemically defined protein-free culture conditions, it is highly desirable to eliminate cholesterol from the culture medium to simplify its formulation as well as to facilitate downstream purification of the expressed product (Sinacore et al., Molecular Biotechnology, 15:249-57, 2000; Gorfien et al., Biotechnol Prog, 16:682-7, 2000). There have been published reports demonstrating slow adaptation of NS0 cells to cholesterol-free (Keen et al., Cytotechnol., 17:203-211, 1995) and protein-free culture conditions (Gorfien et al., Biotechnol Prog, 16:682-7, 2000).

Cholesterol fulfills many key physiological functions in higher organisms. Biological manifestation of cholesterol, its metabolites and biosynthetic intermediates span various cellular and developmental processes, ranging from cellular membrane transport, intracellular signaling, stress response, cancer, and reproductive biology (Simons et al., Nat Rev Mol Cell Biol, 1:31-9, 2000; Liscum et al., Biochim Biophys Acta, 1438:19-37, 1999; Tabas, J Clin Invest, 110:583-90, 2002). The synthesis of cholesterol begins with condensation of three carbon units of acetyl CoA by 3-hydroxy-3-methylglutaryl (HMG)-CoA synthase (HMGCS) to form HMG-CoA as shown in FIG. 1 (Step 1). HMG-CoA is converted to mevalonate by HMG-CoA reductase (HMGCR). Mevalonate is further metabolized to farnesyl-diphosphate by a series of peroxisomal enzymes. These earlier steps in the cholesterol biosynthetic pathway that lead to the formation of isoprene units are shared for the biosynthesis of many other compounds such as heme A, dolichol, isopentenyl-tRNA, etc. The first committed step towards the synthesis of cholesterol occurs in the endoplasmic reticulum and is marked by the formation of squalene (FIG. 1, Step 7). Squalene epoxidase and oxidosqualene cyclase convert linear squalene into cyclic lanosterol. Lanosterol contains a four-ring nucleus characteristic of the steroids, but with three additional methyl groups: 4α, 4β and 14α. The removal of those three methyl groups via oxidative demethylation, combined with destauration and isomerisation reactions, converts lanosterol to lathosterol and finally to cholesterol in mammalian cells.

Conversion of lanosterol to lathosterol (Steps 10 to 19) is a complex pathway in itself. First, the 14α methyl group is removed from lanosterol through an oxidative demethylation reaction catalyzed by lanosterol 14α-demethylase (Cyp51). Subsequent reduction of the C14 double bond by steroid-14-reductase (Tm7sf2) allows for the removal of the second methyl group (4α). Oxidation at C4 by 4 methyl sterol oxidase is followed by oxidative decarboxylation by C3 sterol dehydrogenase (also known as C4 decarboxylase, Sc4 mol). Removal of the last methyl group at C4 is catalyzed by the same set of enzymes responsible for removing the 4α methyl group, (4 methyl sterol oxidase and C3 sterol dehydrogenase) (Risley et al., J Chem Ed, 79:377-384, 2002; Gaylor, Biochem Biophys Res Commun, 292:1139-46, 2002) but not until the 3-keto group has been reduced to a hydroxyl group by 3-ketoreductase (Hsd17b7, Step 14). As the last methyl group is removed, the 3-hydroxyl group is again reduced to a keto group. Reduction of this 3-keto group to the β-hydroxy sterol by the same 3-ketoreductase (Step 17) completes the conversion of lanosterol to zymosterol.

Reactions downstream of zymosterol that convert it to cholesterol proceed via two alternative pathways (FIG. 1). The two pathways differ mainly in the point at which Δ24 is reduced. One pathway (Steps 18 to 21) involves reduction of the Δ24 double bond in zymosterol first, followed by Δ8, Δ7 isomerisation to give lathosterol and then cholesterol. The alternative pathway (Steps 18*a* to 21*a*) involves isomerization and desaturation of zymosterol first to give 7-dehydrodesmosterol which is further metabolized to cholesterol. Given the presence of both lathosterol and desmosterol in mammals, the exact sequence of steps downstream of zymosterol have been speculated to be tissue specific (Liscum, in Biochemistry of Lipids, Lipoproteins and Membranes (4th Edition), Ed. Vance et al., Elsevier Science B.V. 2002).

Cloning of genes encoding enzymes in cholesterol biosynthesis has greatly facilitated elucidation of the pathway as well as its regulation (Bach et al., Prog Lipid Res, 36:197-226, 1997). 17β-hydroxysteroid dehydrogenase type 7 (Hsd17b7) was the last gene of the mammalian cholesterol biosynthesis pathway to be cloned and characterized. Hsd17b7 had originally been described as an estrogenic hydroxysteroid dehydrogenase regulating the biological potency of steroids in mammals. It was not until recently, that its role as the 3-ketoreductase of the cholesterol biosynthesis pathway was reported via functional complementation of the mammalian gene in a yeast strain deficient of 3-ketoreductase in its ergosterol biosynthetic pathway (Marijanovic et al., Mol Endocrinol, 17:1715-25, 2003). In this study we demonstrate the role of Hsd17b7 in the inherently cholesterol auxotrophic mammalian cell line, NS0. Identification of the metabolic block leading to cholesterol auxotrophy in NS0 cells and its alleviation by over expression of Hsd17b7 is described in this report.

Materials and Methods

Cells and cell culture. NS0 and NS0_r, the cholesterol independent revertant, were obtained from Pfizer, Inc. (St. Louis, Mo.) and have been described previously (Seth et al., Biotechnol Bioeng, 90:552-67, 2005). Growth response of NS0 cells to various cholesterol biosynthesis pathway precursors and intermediates was studied in CD Hybridoma medium (Invitrogen, Carlsbad, Calif., USA) without cholesterol-lipid concentrate. Growth responses were ascertained in 24-well plates in the presence of six different precursors, each at three different concentrations: citrate (0.01, 0.05, 0.10 mg/ml); mevalonolactone (0.1, 1.0, 5.0 μg/ml); squalene (0.1, 1.0, 5.0 μg/ml); lanosterol (0.1, 1.0, 5.0 μg/ml); lathosterol (0.1, 1.0, 5.0 μg/ml) and 7-dehydrocholesterol (0.1, 1.0, 5.0 μg/ml). Each well containing 1.5 ml precursor-supplemented medium was seeded with $2 \times 10^5$ cells/ml. NS0 cells cultured in the presence of cholesterol served as the positive control. Different intermediates were dissolved in 100% ethanol and added to the culture medium along with 4 mg/ml fatty acid-free BSA (Sigma, St. Louis, Mo., USA). The final concentration of ethanol in the cell culture medium did not exceed 0.5%. Citric acid anhydrous, mevalonolactone, squalene, lanosterol, lathosterol, 7-dehydrocholesterol and cholesterol powder were purchased from Sigma (St. Louis, Mo., USA). All test conditions were performed in duplicate. The medium was supplemented with 4 mg/ml fatty acid-free BSA. Presence of BSA facilitates uptake of the sterol precursors (Sato et al., Mol Biol Med, 2, 121-34:1984).

Reverse transcription and real-time comparative quantitative PCR. Cells in exponential growth phase were harvested and total RNA was extracted from cell samples using the RNeasy Mini Kit (Qiagen, Valencia, Calif., USA) according to the manufacturer's protocol. The purity and integrity of the RNA was verified by running 5 μl sample on a 1.4% agarose gel in 10 mM sodium phosphate buffer, pH 6.8 at 100 V and staining with ethidium bromide (0.5 μg/ml) (Pelle et al., Nucleic Acids Res, 21:2783-4, 1993).

Reverse transcription of RNA was performed according to the Superscript™ II RNase H⁻ Reverse Transcriptase (Invitrogen) protocol using oligo-dT primer. Primers (Table 1) were designed using Array Designer 2 software (PREMIER Biosoft International, Palo Alto, Calif., USA). Amplicon size and reaction specificity were confirmed by agarose gel electrophoresis. SYBR® Green I dye was used to detect the PCR products using QuantiTect SYBR Green PCR kit (Qiagen). Real-time PCR was performed using an ABI 7700 (Applied Biosystems, Foster City, Calif., USA). The reaction was started by incubating the samples at 94° C. for 15 min, followed by 40 cycles of 94° C. for 15 s, 60° C. for 30 s and 72° C. for 30 s. A threshold of 10-fold the average standard deviation of the fluorescent level of the baseline cycles was used to determine $C_T$ (threshold cycle number). Each sample for a given primer pair was analyzed in duplicate. β-actin was used as the normalization message. β-actin is expressed at moderately abundant levels in most cell types and has previously been used as a quantitative reference for RT-PCR assays (Kreuzer et al., Clin Chem, 45:297-300, 1999). The fold-change between the two different cell types was calculated as the ratio of their normalized mRNA levels (Pfaffl et al., Nucleic Acids Res, 29, e45: 2002-2007, 2001). The fold change is equal to $2^{-\Delta\Delta C_T}$, where $\Delta\Delta C_T = \Delta C_{T,NS0} - \Delta C_{T,NS0\_r}$ and $\Delta C_T = C_{T,X} - C_{T,R}$ for a given cell is the difference in threshold cycles between the probed gene and normalizing gene.

pcDNA-Hsd plasmid construction. A full-length mouse cDNA clone for Hsd17b7 was obtained from Open Biosystems (Huntsville, Ala.). The expression plasmid for Hsd17b7 was constructed by isolating a Sma I to BsrG I fragment containing the 1076 bp ORF from the full length clone and subcloning it into pNEB193 between Acc65 I and Pme I. The insert was then isolated and ligated into pcDNA3.1 (+) vector (Invitrogen) between EcoRI and Hind III. The integrity of the resulting plasmid, pcDNA-Hsd was confirmed by restriction mapping and DNA sequencing. Larger amounts of plasmid were extracted from shaker flask cultures using the Qiagen Plasmid Maxi Kit (Qiagen) as per manufacturer's protocol.

Cell transfection. pcDNA-Hsd was transfected into cholesterol-dependent NS0 cells by electroporation. Parallel transfection was carried out with plasmid pcDNA 3.1 (+) as the control. Before electroporation, 40 μg of both pcDNA-Hsd and pcDNA 3.1 (+) was linearized with Bgl II (New England Bioabs, Inc., Beverly, Mass., USA) by incubating for 2 hrs at 37° C. The linearized DNA was analyzed on a 1% (w/v) agarose gel in 1×TAE buffer with ethidium bromide (0.5 μg/ml). After precipitation with ethanol, the DNA pellet was resuspended in 40 μl autoclaved water and transferred to 0.4 cm-gapped electroporation cuvette (BioRad Laboratories, Hercules, Calif., USA).

Cells in the early exponential phase were used for electroporation. Around $10 \times 10^6$ cells were electroporated using BioRad's Gene Pulser II at 3 μF and 1.5 kV. A two-pulse protocol was used and the cells were incubated at room temperature for 1 minute after the first pulse. Electroporated cells were incubated on ice for about 10 minutes after the second pulse, and then transferred to a T-75 flask containing maintenance media supplemented with 10% FBS (Atlas Biologicals, Fort Collins, Colo., USA). This was followed by incubation at 5% $CO_2$ and 37° C. for 24 hours. Cells were also electroporated with eGFP-N1 (BD Biosciences Clontech, Palo Alto, Calif., USA) to determine the efficiency of gene transfer in NS0 cells by flow cytometry. We observed 30% transfection efficiency in NS0 cells with eGFP-N1.

Limiting dilution screening for cholesterol independent pcDNA-Hsd transfectant clones. Limiting dilution plating (Coller et al., Meth Enzymol, 121:412-7, 1986) was carried out for both pcDNA-Hsd and pcDNA transfected cells in 96-well plates. The cells were incubated in non-selective medium for 24 hours and then washed twice in cholesterol-free medium. The cell pellet was resuspended in selective medium containing Geneticin (G418) and aliquoted into 15 96-well cell culture plates @2000 cells/well for both pcDNA-Hsd and pcDNA transfected cells. Untransfected parental NS0 cells were also plated in basal medium (cholesterol-free, G418-free medium) in order to isolate any background cholesterol independent variants in the cell population. The plates were incubated at 5% $CO_2$, 37° C. and saturated humidity for 2-3 weeks. The plates were supplemented with selective medium every 7 days to maintain selective pressure and account for losses in volume due to evaporation.

Results

Figure 2:
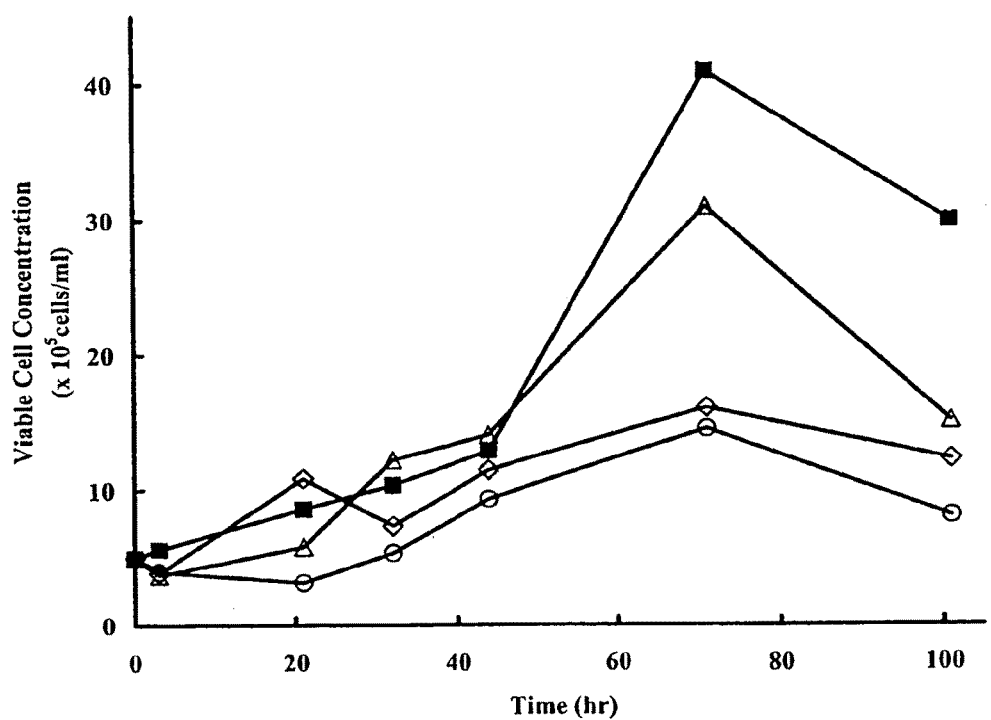
FIG. 2 shows (a) growth response of NS0 cells in 24-well plates in the presence of different intermediates in the cholesterol biosynthesis pathway; and (b) Growth characteristics of NS0 cells in tissue culture flasks in the absence of cholesterol (○), in the presence of 5 μg/ml cholesterol (Δ), 5 μg/ml lanosterol (■) and 5 μg/ml lathosterol (◇). The medium in all four flasks was supplemented with 4 mg/ml fatty acid-free BSA.

Cholesterol Biosynthesis is Blocked at the Conversion of Lanosterol to Lathosterol in NS0 Cells The cholesterol auxotrophy of NS0 cells can possibly be caused by insufficient flux due to limitation of precursor supply or by a blockage in the biosynthetic pathway. In order to identify such a functional block, NS0 cells were cultured in medium supplemented with different precursors or intermediates that lead to the synthesis of cholesterol (FIG. 1) as described in Materials and Methods. Only lathosterol and the intermediates downstream of it were able to support the growth of cells (FIG. 2a). Growth was not supported in wells supplemented with citrate, mevalonolactone, squalene or lanosterol (FIG. 2a). These results indicate that cholesterol biosynthesis in NS0 cells is limited by the formation of lathosterol from lanosterol.

In order to verify the block between lanosterol and lathosterol in the cholesterol biosynthetic pathway, growth kinetics of NS0 cells in the presence of lanosterol (5.0 µg/ml), lathosterol (5.0 µg/ml) and cholesterol (5.0 µg/ml) were determined. Cells were also grown in basal medium supplemented with fatty acid-free BSA only (FIG. 2b). Lanosterol and BSA alone were unable to support the growth of NS0 cells, while lathosterol was effective in promoting the growth of NS0 cells. Cells attained a maximum cell density of $4 \times 10^6$ cells/ml after 70 hrs in culture with lathosterol, compared to $3 \times 10^6$ cells/ml in medium supplemented with cholesterol. These observations were consistent over repeated cultures. The results support the notion that the block between lanosterol and lathosterol in the biosynthesis of cholesterol in NS0 is at least partly responsible for cholesterol auxotrophy in this cell line.

Expression Profile of Genes Encoding Enzymes in the Cholesterol Biosynthesis Pathway We further investigated the mechanism of cholesterol deficiency in NS0 cells at the transcript level by using real-time quantitative PCR to determine relative message levels of enzymes in the cholesterol biosynthesis pathway, including the 7 enzymes involved in the conversion of lanosterol to lathosterol. Average $C_T$ values (threshold cycle number) obtained for NS0 along with the standard deviation are reported in Table 2. We compared NS0 cells, cultivated under standard cholesterol-dependent growth conditions, to cells adapted to cholesterol independent conditions (NS0 revertant, NS0_r). The ratio of transcript levels between NS0 and NS0_r was calculated using comparative $C_T$ method (ABI-Prism 2001). The cholesterol biosynthesis machinery is distributed among a number of organelles: the cytosol, peroxisome and endoplasmic reticulum (ER). HMGCS catalyzing the condensation of acetyl-CoA to HMG-CoA is found in the cytosol. However, different isoforms of the same enzyme, (such as HMGCS, HMGCR) may reside in more than one cellular compartment (Liscum et al., Biochim Biophys Acta, 1438:19-37, 1999). Among the genes whose transcripts were measured (Table 2), starting from hydroxymethyl glutaryl-CoA reductase (Hmgcr) through 7-dehydrocholesterol reductase (Dhcr7), 5 genes encode enzymes that reside in the peroxisome and the other 12 genes encode enzymes present in the ER.

Included among the messages measured is the Hsd17b7 message, encoding the 3-ketoreductase that was originally identified as a protein oxidizing or reducing steroid hormone in mammals but recently shown to functionally complement ERG27 deficient yeast and hence participate in cholesterol biosynthesis. The $C_T$ value provides a measure of relative abundance of these messages, with a lower $C_T$ value corresponding to a higher level of relative message abundance. The results indicate that the majority of transcripts assayed are present at about 16 (Sc4mol) to 125 times lower than the normalization transcript (β-actin); exceptions are Lss and Hsd17b7 which are present at much lower levels than the others. Comparative transcript analysis revealed down-regulation of most of the genes in the post squalene segment of the pathway in the revertant cell line NS0_r. Out of the seven enzymes involved in the conversion of lanosterol to lathosterol, four (Cyp51, Nsdhl, Ebp, Dhcr24) are down-regulated in the revertant. Two (Tm7sf2, Sc4 mmol) may be slightly up-regulated or unchanged, since the difference in $C_T$ values between NS0 and NS0_r is within two standard deviations from the average value $C_T$ value for NS0. Among all the transcripts assayed, Hsd17b7 is the only message that is up regulated significantly in NS0_r. Therefore, Hsd17b7 is clearly noticeable among those messages, not only due to its low expression level in wild type cells, but also due to its 15-fold up regulation in the revertant.

Over Expression of Hsd17b7 in NS0 Cells

Results from the precursor/intermediate feeding experiment described above suggest that a block(s) exists in the steps before lathosterol in the NS0 cholesterol biosynthesis pathway. Because they were expressed at the lowest level, we suspected that low levels of oxidosqualene cyclase (Lss) and hydroxysteroid (17-beta) dehydrogenase 7 (Hsd17b7) might be responsible for the observed cholesterol auxotrophy. The fact that only Hsd17b7 is substantially up-regulated in the revertant suggests that Hsd17b7 is the missing or blocked step in converting lanosterol to lathosterol in NS0. Lss, in spite of being expressed at a low level in the wild type NS0, is expressed in NS0_r at similar transcript level. To explore the possibility that it is the limiting step in cholesterol biosynthesis in NS0 cells, we over expressed the Hsd17b7 gene in transfection experiments. We constructed an expression plasmid, pcDNA-Hsd, containing Hsd17b7 transcriptionally regulated by the CMV early promoter on a pcDNA 3.1 (+) plasmid backbone. After electroporating NS0 cells with linearized preparations of pcDNA 3.1 (+) plasmid (control) and pcDNA-Hsd, transfectants were selected in the absence of cholesterol and in the presence of 300 µg/ml G418. 14 clones were isolated after limiting dilution plating of pcDNA-Hsd transfected cells. Only a single clone survived in the plates that were seeded with cells transfected with the control plasmid (pcDNA). There were no surviving clones in the untransfected cell population that was plated in the absence of cholesterol, indicating low background frequency (about $10^{-6}$) of cholesterol independence.

The cholesterol independent phenotype of clones isolated after pcDNA-Hsd transfection as well as the control plasmid transfection was confirmed by maintenance for over twenty passages in cholesterol-free medium.

Characterization of Hsd17b7 Stable Transfectants

Figure 3:
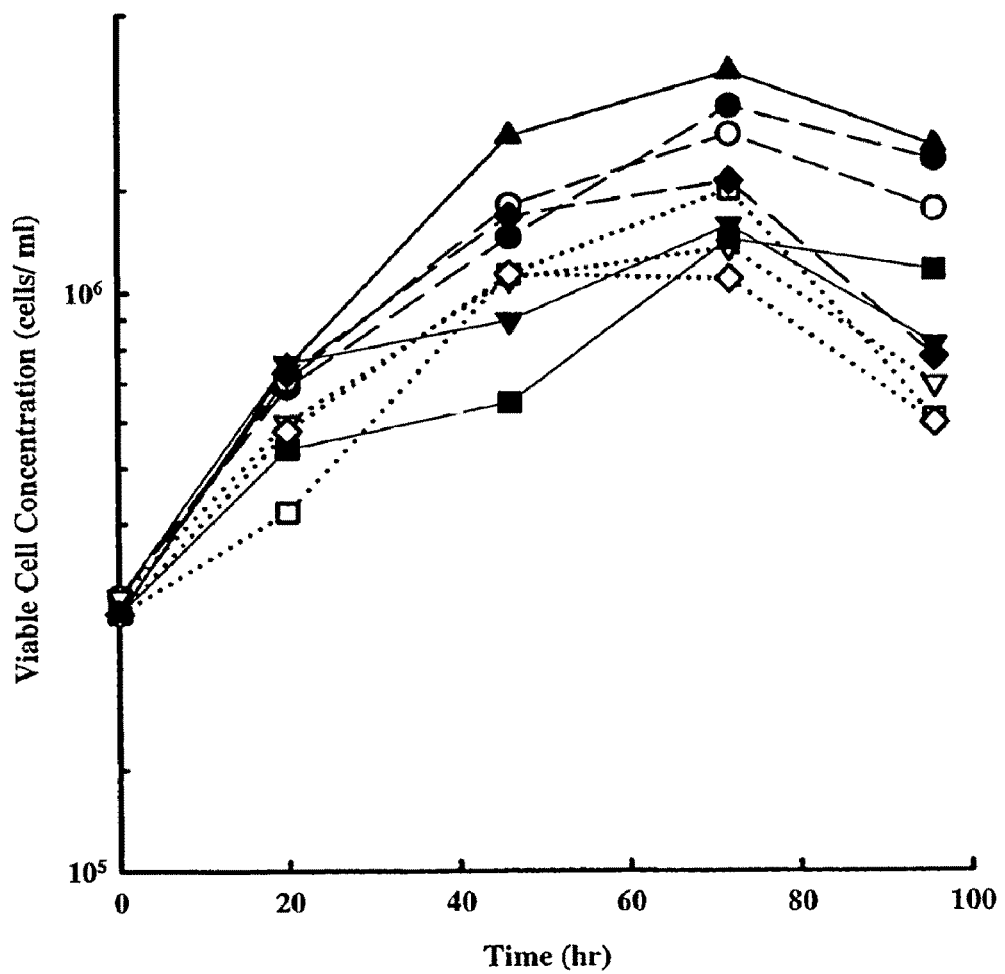
FIG. 3 shows growth characteristics of pcDNA-Hsd transfectants: clones 5B2 (●), 8D5 (○), 12D1 (▼), 6G9 (∇), 11D4 (●), 9G2 (□), 6F5 (♦), the control plasmid transfectant 12G9_pcDNA (◇); and the natural revertant NS0_r (▲). All these cells were cultured in the absence of cholesterol.

Seven pcDNA-Hsd transfectant clones (5B2, 8D5, 12D1, 6G9, 11D4, 9G2 and 6F5) and the single pcDNA clone (12G9_pcDNA) were further characterized. These cells were maintained in the absence of cholesterol. The growth rates and maximum cell density achieved in culture vary among these clones (FIG. 3). While both 5B2 and 8D5 were able to grow to a density of approximately $2 \times 10^6$ cells/ml, 12G9_pcDNA from the control plasmid transfection grew slower and reached a maximum cell density of only about $1 \times 10^6$ cells/ml. The natural revertant, NS0_r, also maintained in the absence of cholesterol, exhibited a faster growth rate and was able to attain higher cell density.

The transcript level of Hsd17b7 in the cholesterol independent transfectant clones was assessed by quantitative real-time PCR. To better present the changes in Hsd17b7 expression levels in those clones, and to examine the possible effect of transfection on the expression of other genes in the pathway, expression of Hmgcr, encoding a key cholesterol biosynthesis enzyme (FIG. 1, Step 2) was also examined. Table 3 summarizes the results of real-time PCR analysis.

Hsd17b7 expression was substantially higher in all pcDNA-Hsd transfectants compared to the natural revertant, NS0_r. This can be attributed to the presence of a strong and constitutive CMV promoter upstream of Hsd17b7 on the pcDNA-Hsd construct. The extent of up-regulation was highest (about 500 fold) in 5B2. The control plasmid transfected clone, 12G9_pcDNA had Hsd17b7 expression level similar to NS0_r. The observed variation among the different clones is not unexpected given the expected heterogeneity in transgene copy number and random integration of plasmid DNA into host chromosome.

Overall, there did not appear to be any direct correlation between growth rate and Hsd17b7 transcript level among the different clones, although in the specific case of 5B2 the highest level of Hsd17b7 expression was accompanied by the fastest growth rate (FIG. 3). In comparison to Hsd17b7, Hmgcr levels remained fairly consistent among the clones. Except for clones 8D5 and 6G9, for which Hmgcr is down regulated about 7-fold, other clones exhibited moderate to low levels of down regulation compared to NS0_r. Taken as a whole, there did not seem to be any drastic effect of pcDNA-Hsd transfection on the endogenous expression level of Hmgcr.

Discussion

In this study we demonstrated that the cholesterol auxotrophy of NS0 cells is caused by a metabolic block in the conversion of lanosterol to lathosterol, a segment of the cholesterol biosynthesis pathway that involves the removal of three methyl groups as shown in FIG. 1. The demethylation reaction at position 4C results in a keto group at position 3 of the substrate that is reduced to a 3β-hydroxyl by a 3-ketoreductase. 3-ketoreductase is utilized twice in the pathway; initially, for the reduction of 4-methylzymosterone to 4α-methylzymosterol and again for the 3-ketoreduction of zymosterone to zymosterol. This 3-ketoreductase was the last enzyme to be identified and characterized for ergosterol biosynthesis in yeast and was designated ERG27 (Gachotte et al., Proc Natl Acad Sci USA, 96:12655-60, 1999). Through functional complementation in an ergosterol auxotrophic yeast mutant, the mouse ortholog of ERG27, Hsd17b7, was also shown to catalyze the same reaction (Marijanovic et al., Mol Endocrinol, 17:1715-25, 2003). Similar to Hsd17b7, functional characterization of several other mammalian cholesterol biosynthetic pathway genes has relied on complementation analysis of mutations in yeast sterol auxotrophs (Hanner et al., J Biol Chem 270(13):7551-7, 1995; Li et al., J Biol Chem 271(28):16927-33, 1996; Moebius et al., Proc Natl Acad Sci USA 95(4):1899-902, 1998; Nishi et al., Biochim Biophys Acta 1490(1-2):106-8, 2000; Sakakibara et al., J Biol Chem 270(1):17-20, 1995). Ideally, the functional characterization of mammalian genes should be performed in mammalian cells. However, suitable mammalian cell mutants lacking the specific enzyme in the pathway are often not available.

Through metabolic studies it has previously been shown that NS-1 cells, the parental cell from which NS0 was derived, is blocked in the conversion of lanosterol to lathosterol; further, through the identification of an accumulated C-28 intermediate (4α-methyl-cholesten-3-one), the block was proposed to be due to the 3 ketoreductase (Sato et al., In Vitro Cell Dev Biol, 24:1223-8, 1988). However, no studies have been reported since then to further elucidate this block in NS-1 cells.

In our transcriptional analyses using quantitative RT-PCR we showed that the Hsd17b7 transcript is present at a very low level in cholesterol auxotrophic NS0 but is increased by about 15-fold in a natural revertant, NS0_r. We have previously examined the gene expression profile of NS0 and NS0_r by using Affymetrix microarray, MGU74Av2, and reported a similar overall down-regulation of genes encoding ER enzymes in the revertant cell line NS0_r. Genes that were down regulated greater than 2-fold in the microarray analyses included Lss, Dhcr7, Sqe and Cyp51. The spot corresponding to Hsd17b7 on the Affymetrix array had low signal strength for both NS0 and NS0_r and was filtered out during analysis due to its weak detection call (Seth et al., Biotechnol Bioeng, 90:552-67, 2005). The cholesterol requirement in NS0 is thus likely to be the result of a blocked biosynthetic pathway due to a deficiency of Hsd17b7.

Hsd17b7 belongs to the family of 17β-hydroxysteroid dehydrogenases (17β-HSD). As a family, 17β-HSD is comprised of eleven different enzymes that catalyze conversion of the keto group on the $17^{th}$ carbon in steroids to their 17β-hydroxy forms (Payne et al., Endocr Rev, 25:947-70, 2004). Steroids are present in the inactive keto form in vivo, and are converted to the corresponding functionally active hydroxy form when needed. These 17β-HSD enzymes are involved in the final step that leads to the formation of active steroid hormones like estradiol and testosterone. 17β-HSD may also play a role in metabolizing substrates such as fatty acids and retinols (Adamski et al., Mol Cell Endocrinol, 171:1-4, 2001). The members of this family differ in their substrate specificities, are found in different types of tissues and exhibit different mechanisms of regulation. The different numbers for each of these enzymes represent the chronological order in which they were identified. Hsd17b7 was originally described as the prolactin-receptor associated protein (PRAP) in rats (Duan et al., Endocrinol, 138:3216-21, 1997) and was known to catalyze the transformation of estrone to estradiol by converting the 17-keto group to a 17-hydroxy group as part of steroid metabolism, using NADPH as a cofactor. Relative catalytic efficiencies of mouse Hsd17b7 for estrone and estradiol indicate that estrone is the preferred substrate for this enzyme (Nokelainen et al., Mol Endocrinol, 12:1048-59, 1998). Rat and mouse Hsd17b7 was reported to be most abundantly expressed in the ovaries of pregnant animals and was responsible for increasing levels of estradiol production in the corpus luteum. Small amounts of Hsd17b7 could be detected in the ovaries of adult non-pregnant mice, in the mammary gland, liver, kidney, and testis (Nokelainen et al., Mol Endocrinol, 12:1048-59, 1998). Later, Hsd17b7 was shown to be strongly expressed in HepG2 hepatoma cells (Krazeisen et al., FEBS Lett, 460:373-9, 1999) and in the liver of marmost monkeys (Husen et al., Mol Cell Endocrinol, 171:179-85, 2001). The presence of Hsd17b7 in liver was unexpected since it is the site for estradiol inactivation. As speculated by Breitling et al. (Mol Cell Endocrinol, 171:199-204, 2001), the detection of estrogenic Hsd17b7 in the liver could be explained by a local effect of estradiol production or by the possibility that Hsd17b7 in the liver recognizes a different substrate. Subsequent homology and structural analyses (Breitling et al., Mol Cell Endocrinol, 171:199-204, 2001) revealed the similarity of Hsd17b7 to the yeast 3-ketoreductase. Also, functional analyses of human and mouse Hsd17b7 revealed that both could catalyze the conversion of estrone to a more potent estrogen, estradiol, and of dihydrotestosterone, a potent androgen, to an estrogenic metabolite 5α-androstane-3α,17β-diol (3αA-diol) and to a lesser degree 3βA-diol, thereby catalyzing the reduction of the keto group in either 17- or 3-position of the substrate (Torn et al., Biochem Biophys Res Commun, 305:37-45, 2003). Dual activity has also been observed for Hsd17b2 (3α/17β) (Suzuki et al., J Clin Endocrinol Metab, 85:3669-72, 2000) and 3αHsd type 2 (Hsd17b5) (3α/17β) (Lin et al., Mol Endocrinol, 11:1971-84, 1997). Therefore, the role of Hsd17b7 in catalyzing 3-ketoreduction was plausible. Also, in their studies of regulation mediated by sterol regulatory element binding protein (SREBP), Horton et al observed that in the livers of transgenic mice expressing nuclear forms of SREBP-2, Hsd17b7 was over expressed approximately 9-fold (average value from duplicate microarray hybridizations) (Horton et al., Proc Natl Acad Sci USA, 100:12027-32, 2003). Since the regulatory effect of SREBP-2 has been expected to be limited to cholesterol biosynthesis (Horton et al., J Clin Invest, 101: 2331-9, 1998), the increased level of Hsd17b7 on SREBP-2 expression led the authors to speculate that Hsd17b7 is a candidate for direct SREBP-2 mediated regulation and might play a role in cholesterol biosynthesis.

Marijanovic et al. demonstrated the ability of Hsd17b7 to convert zymosterone to zymosterol using NADPH as the cofactor in vitro. They also reported functional complementation by mammalian Hsd17b7 gene in ERG27-deficient yeast strain, restoring its growth in cholesterol-deficient medium (Marijanovic et al., Mol Endocrinol, 17:1715-25, 2003). The authors proposed Hsd17b7 to be the mammalian ortholog of yeast 3-ketoreductase (ERG27), thereby implicating its role in cholesterogenesis.

The mouse Hsd17b7 gene is present on chromosome 1. Its cDNA encodes a 334 amino acid protein with a calculated mass of 37.3 kDa (Nokelainen et al., Mol Endocrinol, 12:1048-59, 1998). Detailed structural analysis of mouse Hsd17b7 genes has not been reported. However, the genomic structure of human Hsd17b7 has been analyzed and it is reported to be a 21.8 kb gene consisting of 9 exons and 8 introns (Krazeisen et al., FEBS Lett, 460:373-9, 1999). Krazeisen et al. reported the gene to be located on chromosome 10p11.2, while a more recent report (Torn et al., Biochem Biophys Res Commun, 305:37-45, 2003) identified the human Hsd17b7 on chromosome 1q23. Human Hsd17b7 cDNA encodes a 37-kDa protein that shows 78% and 74% amino acid identity with rat and mouse, respectively (Krazeisen et al., FEBS Lett., 460:373-9, 1999).

Although we can conclude that the cholesterol dependency in NS0 is caused by the lack of Hsd17b7 expression, the mechanism of Hsd17b7 deficiency is incompletely understood. The natural revertant (NS0_r) used in this study was obtained by slow adaptation of wild type NS0 cells, gradually decreasing cholesterol content in the culture medium over time. Genetically, this results in 15-fold elevation of Hsd17b7 transcript level in NS0_r compared to the wild type NS0 cells. Barring the unlikely event of gene amplification, this increased expression of endogenous Hsd17b7 is possibly the result of epigenetic modifications of the regulatory region of the endogenous gene while the cells were undergoing selection under cholesterol-free culture conditions. This would lead one to suspect epigenetic gene silencing as the likely cause of Hsd17b7 deficiency.

The transfectants of pcDNA-Hsd isolated in this study exhibit a wide range of transcript expression level of Hsd17b7. Comparison of the transcript data with their growth profile indicates that clones with a higher growth rate similar to that of the natural revertant, NS0_r also have substantially higher levels of Hsd17b7 transcript compared to NS0_r. With the limited number of clones analyzed it is not possible to conclude whether the transcript levels actually correlate to growth rate of the clones. It is also known that transcript levels do not necessarily correlate to protein expression levels. Regulation of gene expression at the translational level (Stover, Nutr Rev, 61:427-31, 2003; Holcik et al., Nat Rev Mol Cell Biol, 6:318-27, 2005) may negate the effect of higher transcript levels. The results appear to suggest that other such mechanisms may be at play in regulating the expression of Hsd17b7.

In this example, we demonstrated that the additional presence of exogenous Hsd17b7 reversed the cholesterol dependence of NS0 cells. These results further affirm the role of Hsd17b7 in cholesterogenesis in a mammalian cell. As mentioned above, this enzyme has also previously been shown to catalyze the conversion of steroid estrone to estradiol. The finding that the same enzyme plays a key role both in cholesterol synthesis and in steroid activation poses an interesting question. How are the cholesterol and steroid synthesis pathways regulated independently while sharing the same enzyme? In vivo, while most cholesterol synthesis occurs in the liver and some in the neural tissue, estradiol production occurs mainly in the ovary. Little synthesis of cholesterol occurs in reproductive organs (Christenson et al., Reprod Biol Endocrinol, 1:90, 2003). This compartmentalization in different tissues may provide functional separation of Hsd17b7. One would also anticipate tissue-specific regulation of both Hsd17b7 functions, one responding to the presence of nuclear SREBP-2 for cholesterol biosynthesis and the other responding for steroid control. Structurally, homology-based molecular modeling of Hsd17b7 reveals a conserved loop C-terminal of the NAG-motif at the substrate-binding site, and a hydrophobic helix that is part of the (α/β)-core of the dehydrogenase structure (Breitling et al., Mol Cell Endocrinol, 171:199-204, 2001). More detailed studies are needed to elucidate the domain structure and regulatory mechanism underlying Hsd17b7 activity.

Through transcriptional analyses, this study has elucidated for the first time the specific role of Hsd 17b7 in the cholesterol biosynthesis pathway in mammals and in relieving cholesterol auxotrophy of NS0 cells. This functional characterization of Hsd17b7 not only contributes to our understanding of sterol biosynthesis, but may also provide a new target for developing antagonists for cholesterol biosynthesis. Given the economic importance of NS0 in producing therapeutic antibodies, elucidation of the mechanism of its cholesterol dependence is especially noteworthy. This will provide a rational way of reverting cholesterol dependence of recombinant NS0 cells and ease the cultivation process for producing antibodies.

Tables

TABLE 1

Sequences of primers used for PCR amplification of cholesterol biosynthesis genes

| Probe | Forward Primer | Reverse Primer |
| --- | --- | --- |
| Hydroxymethylglutaryl-CoA reductase (HMGCR) | GCCGTCATTCCAGCCAAG (SEQ ID NO: 2) | CGTTGTAGCCGCCTATGC (SEQ ID NO: 3) |
| Mevalonate kinase (Mvk) | GGTCTCCGTCAGCAGGTG (SEQ ID NO: 4) | GCATTGTCCACACCAGAAGG (SEQ ID NO: 5) |
| Phosphomevalonate kinase (PMvk) | AAGATTGTGGAAGGCGTGTC (SEQ ID NO: 6) | CACTACTCGGACTGTCTGTATC (SEQ ID NO: 7) |
| Isopentenyl-diphosphate delta-isomerase (IPP) | TCAGTGTACCATGATTGCCTTG (SEQ ID NO: 8) | GAACCTGCTCTGCCTGTTG (SEQ ID NO: 9) |

TABLE 1-continued

Sequences of primers used for PCR amplification of cholesterol biosynthesis genes

| Probe | Forward Primer | Reverse Primer |
|---|---|---|
| Geranylgeranyl diphosphate synthase 1 (Ggps1) | TCATCGTGGAACCGTCAGC (SEQ ID NO: 10) | TGCCTGTGAAAGTTTGCTTCTC (SEQ ID NO: 11) |
| Farnesyldiphosphate farnesyl transferase 1 (Fdft1) | AAGGATGGAGTTCGTCAAGTG (SEQ ID NO: 12) | GCTGCTGCTGAGTGAGTC (SEQ ID NO: 13) |
| Squalene epoxidase (Sqe) | CCTTCCTACCGAGCACCTG (SEQ ID NO: 14) | CACACTTCTTCATTCAGCCAAC (SEQ ID NO: 15) |
| Oxidosqualene cyclase (Lss) | GGACTGCCCTGAACTATGTG (SEQ ID NO: 16) | AGGACAGCCAGCCAGAAC (SEQ ID NO: 17) |
| Lanosterol 14alpha demethylase (Cyp51) | AGGTGACAGGAGGCAACTTG (SEQ ID NO: 18) | GGCGAGACGGAACAGGTAG (SEQ ID NO: 19) |
| Steroid 14 reductase (Tm7sf2) | AGTTGCTGTATGTGGGTGATG (SEQ ID NO: 20) | GCAGGCTGTAGGTGAATGG (SEQ ID NO: 21) |
| Sterol C4 methyl oxidase-like (Sc4mol) | AGAATACGCACATCCCTTGG (SEQ ID NO: 22) | GCGGGTTGAGAGGAATATCA (SEQ ID NO: 23) |
| C3 sterol dehydrogenase (Nsdhl) | GATGCCAACGACCCTAAGAA (SEQ ID NO: 24) | AACCACATTCTCCACGAAGG (SEQ ID NO: 25) |
| 3 ketoreductase (Hsd17b7) | TGGCAGAAGACGATGACCTC (SEQ ID NO: 26) | GGCAGGATTCCAGCATTCAG (SEQ ID NO: 27) |
| Phenylalkylamine $Ca^{2+}$ antagonist (amopamil) binding protein (Ebp) | ATCTTCTTCCTCCTCGCACAG (SEQ ID NO: 28) | CCTCAGGTTCCTAGCAGTAGC (SEQ ID NO: 29) |
| 24-dehydrocholesterol reductase (Dhcr24) | GAGACACTACTACCACCGACAC (SEQ ID NO: 30) | CACCATCCAGCCGAAGAGG (SEQ ID NO: 31) |
| Sterol-C5-desaturase (Sc5d) | CAAGTGACAGACACAACCATTG (SEQ ID NO: 32) | GGCTGGATATACATACGGAGTG (SEQ ID NO: 33) |
| 7-dehydrocholesterol reductase (Dhcr7) | TCCAAGAAGGTGCCATTACTC (SEQ ID NO: 34) | AGGATAAGAGGTAAGCGTTCAC (SEQ ID NO: 35) |
| sterol O-acyltransferase (Soat) | AGCACTGTCCTCTGAAGAACC (SEQ ID NO: 36) | GACGGCTGGCTCGGAATC (SEQ ID NO: 37) |
| β-actin | TGTCCACCTTCCAGCAGATG (SEQ ID NO: 38) | GCTCAGTAACAGTCCGCCTAG (SEQ ID NO: 39) |

TABLE 2

Transcript level of cholesterol biosynthesis genes from real-time PCR analysis

| Gene Description | $C_T$ value for NS0 wild type | Fold Change in revertant NS0_r* |
|---|---|---|
| Hydroxymethylglutaryl-CoA reductase (HMGCR) | 20.1 ± 0.2 | (+)1.4 |
| Mevalonate kinase (Mvk) | 23.2 ± 0.0 | (+)1.4 |
| Phosphomevalonate kinase (PMvk) | 22.3 ± 0.3 | (−)1.2 |
| Isopentenyl-diphosphate delta-isomerase (IPP) | 20.7 ± 0.3 | (+)2.9 |
| Geranylgeranyl diphosphate synthase 1 (Ggps1) | 23.3 ± 0.2 | (+)1.3 |
| Farnesyldiphosphate farnesyl transferase 1 (Fdft1) | 21.3 ± 0.3 | (−)2.1 |
| Squalene epoxidase (Sqe) | 20.7 ± 0.1 | (−)1.3 |
| Oxidosqualene cyclase (Lss) | 25.1 ± 0.6 | (−)1.6 |
| Lanosterol 14alpha demethylase (Cyp51) | 19.4 ± 0.2 | (−)1.5 |
| Steroid 14 reductase (Tm7sf2) | 20.5 ± 0.2 | (+)1.3 |
| Sterol C4 methyl oxidase-like (Sc4mol) | 17.9 ± 0.2 | (+)1.2 |
| C3 sterol dehydrogenase (Nsdhl) | 18.6 ± 0.1 | (−)2.1 |
| Hydroxysteroid (17-beta) dehydrogenase 7 (Hsd17b7) | 25.4 ± 0.6 | (+)14.9 |
| Phenylalkylamine $Ca^{2+}$ antagonist (amopamil) binding protein (Ebp) | 21.6 ± 0.3 | (−)1.4 |
| 24-dehydrocholesterol reductase (Dhcr24) | 21.3 ± 0.3 | (−)4.9 |
| Sterol-C5-desaturase (Sc5d) | 23.9 ± 0.4 | (+)3.1 |
| 7-dehydrocholesterol reductase (Dhcr7) | 22.9 ± 0.0 | (−)1.3 |
| β-actin | 16.0 ± 0.3 | |

*(+)Up-regulation in NS0_r, ratio is NS0_r/NS0
(−)Down-regulation in NS0_r, ratio is NS0/NS0_r

TABLE 3

Transcript level in NS0 transfectants compared to wild type NS0

| | Expression level relative to natural revertant, NS0_r* | |
|---|---|---|
| Clone | Hsd17b7 | Hmgcr |
| 5B2 | (+)496.2 | (−)2.9 |
| 8D5 | (+)15.7 | (−)7.9 |
| 12D1 | (+)119.4 | (−)2.9 |
| 6G9 | (+)31.2 | (−)7.5 |
| 11D4 | (+)8.2 | (−)3.2 |
| 9G2 | (+)16.1 | (−)1.7 |
| 6F5 | (+)26.7 | (−)1.4 |
| 12G9_pcD | (+)1.2 | (−)1.5 |
| NS0_r | 1.0 | 1.0 |

*(+)Up-regulation in Transfectant, ratio is Transfectant/NS0_r
(−)Down-regulation in Transfectant, ratio is NS0_r/Transfectant Example II Reverting Cholesterol Auxotrophy of NS0 Cells by Altering Epigenetic Gene Silencing NS0 is a cholesterol-requiring mouse myeloma cell line widely used in the production of recombinant antibodies. We have previously reported that the deficiency of 17β-hydroxysteroid dehydrogenase type7 (Hsd17b7) is responsible for the cholesterol auxotrophy of NS0 cells. Here we demonstrate DNA methylation to be the mechanism underlying transcriptional suppression of Hsd17b7 in cholesterol dependent NS0 cells. Analysis of the DNA methylation pattern revealed methylation of the CpG-rich region upstream of the Hsd17b7 transcription start site in NS0 cells. This is in contrast to the unmethylated status of this sequence in a naturally isolated cholesterol independent revertant cell population (NS0_r). This transcriptional repression was relieved after treating cells with the demethylating drug, 5-azacytidine. Drug treatment also gave rise to high frequency cholesterol-independent variants. Characterization of revertants revealed substantially elevated transcript level of 17β-hydroxysteroid dehydrogenase type7 (Hsd17b7) gene along with hypomethylation of the CpG-rich region. These results affirm that deficiency of Hsd17b7 causes cholesterol dependence of NS0 cells. Furthermore, induction of cholesterol independence by altering DNA methylation pattern alludes to the role of epigenetics in the metabolic adaptation of NS0 cells. With the widespread use of NS0 cells, this finding will have a significant impact on the optimization of recombinant antibody production processes. See Seth et al., Biotechnol. Bioeng. 93(4):820-7, Mar. 5, 2006.

NS0 is a non-immunoglobulin secreting mouse myeloma cell line that is used frequently as efficient fusion partner for hybridoma generation and as host for expressing recombinant immunoglobulins (Barnes et al., Cytotechnology 32:109-23, 2000; Bebbington et al., Bio/technology 10:169-75, 1992; Chu et al., Curr Opin Biotech 12(2):180-7, 2001; Geisse et al., Prot Exp Purif 8(3):271-82, 1996; Verma et al., J Immunol Meth 216(1-2):165-81, 1998). These cells are cholesterol auxotrophs and have an essential requirement of cholesterol in culture medium (Keen et al., Cytotechnology 17(3):203-11, 1995). However, they can be adapted to cholesterol-independence (Gorfien et al., Biotech Prog 16(5):682-7, 2000), and some cholesterol-independent variants have also been reported in the literature (Birch et al., Cytotechnology 15:11-6, 1994).

In a previous report we investigated the cholesterol dependent phenotype of NS0 cells by comparing the overall gene expression profile of wild type cholesterol dependent NS0 cell population and the adapted, cholesterol-independent cell population (NS0_r) using DNA microarrays (Seth et al., Biotech. Bioeng. 90(5):552-67, 2005). Together with precursor feeding experiments and quantitative transcript analysis, the results suggested a metabolic block along the conversion of lanosterol to lathosterol in the wild type NS0 cells. Deficiency of 17β-hydroxysteroid dehydrogenase type7 (Hsd17b7), an enzyme recently shown to be involved in cholesterol biosynthesis in yeast (Marijanovic et al., Mol Endocrinol 17(9): 1715-25, 2003) was shown to be responsible for the cholesterol auxotrophy. Hsd17b7 encodes a 3-ketoreductase and is utilized twice in the conversion of lanosterol to lathosterol during cholesterol biosynthesis (Risley, J Chem Ed 79(3): 377-84, 2002). In a natural revertant, Hsd17b7 was expressed 15 fold higher compared to the parental wild type cells. Expression of exogenous Hsd17b7 rectified the cholesterol dependency in NS0 cells. However, the mechanism underlying Hsd 17b7 deficiency in NS0 cells was not known.

Here we report epigenetic modification via DNA methylation as the mechanism causing lack of Hsd17b7 expression in NS0 cells. DNA methylation is a post-replicative epigenetic modification that encompasses mitotically and/or meiotically heritable changes in gene function that do not entail a change in DNA sequence (Wu et al., Science 293(5532): 1103-5, 2001). DNA methylation involves addition of a methyl group at the C5 position of the cytosine base in the context of a 5'-CpG-3' dinucleotide, where 'p' denotes the phosphodiester linkage, by DNA methyltransferases. CpG islands are short stretches of DNA with higher G+C content than genome average. There are around 45,000 CpG islands in the human genome and 37,000 in the mouse genome (Antequera et al., Proc Natl Acad Sci USA 90(24):11995-9, 1993). Although these islands are scattered throughout the genome, most are found in the promoter regions of constitutively expressed house-keeping genes. Typically, CpGs found in the CpG islands are non-methylated. However, methylation of these CpG-islands can lead to strong transcriptional repression leading to gene silencing (Antequera et al., Cell 62(3):503-14, 1990). DNA methylation plays a key role in establishing cell type specific gene expression levels and is involved in specific biological processes such as genomic imprinting, cell differentiation, and development (Boyes et al., Cell 64(6): 1123-34, 1991; Egger et al., Nature 429(6990):457-63, 2004; Holliday, Russo et al., Eds., Epigenetic mechanisms of gene regulation: Cold Spring Harbor Laboratory Press, 1996; Laird et al., Hum Mol Genet. 3(Spec No):1487-95, 1994). Aberrant methylation patterns have been observed during tumor development (Robertson et al., Nat Rev Genet 1(1): 11-9, 2000), manifested by an overall decrease in genomic methylation and hypomethylation of anti-apoptosis genes, such as bcl-2 gene, and proto-oncogenes such as, k-ras. Cytosine methylation can also promote oncogenesis via hypermethylation of tumor suppressor genes such as Rb, p16(INK4α), BRCA1 (Herman, Semin Cancer Biol 9(5): 359-67, 1999).

Figure 4:
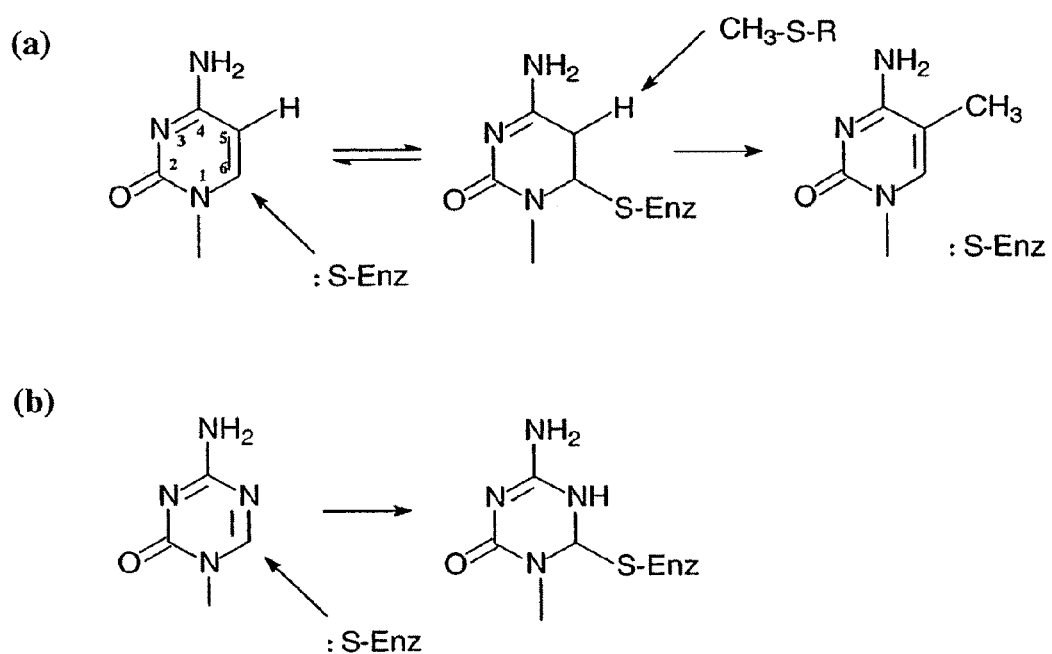
FIG. 4 shows the chemistry of the methylation reaction (Juttermann et al., Proc Natl Acad Sci USA 91(25):11797-801, 1994) (a) methylation of cytosine within the DNA (b) cytosine replaced by analog 5-azacytidine.:S-Enz, cysteine residue of the DNA cytosine-5-methyltransferase enzyme; $CH_3$—S—R, S-adenosylmethionine (methyl donor).

5 azacytidine (5azaC) ($C_8H_{12}N_4O_5$) is a pyrimidine (U, T, C) analogue and is known to induce demethylation in mammalian cells. Typically, methylation of the cytosine residue on DNA involves covalent binding of methyltransferase (MTase) at C6 position. This covalent binding renders C5 susceptible to a nucleophilic attack by the methyl donor, S-adenosylmethionine, leading to transfer of the methyl group to C5. This is followed by the release of the methyltransferase enzyme by β-elimination (Juttermann et al., Proc Natl Acad Sci USA 91(25):11797-801, 1994) (FIG. 4a). When cytosine is replaced by 5azaC in the DNA, C6 still reacts with the cysteine thiolate of MTase, as mentioned above, but C5 methylation does not occur. The MTase enzyme remains covalently bound and cannot be released from the 5azaC substituted DNA (FIG. 4b) leading to an overall decrease in MTase concentration inside the cell and loss of methylation at many sites in the genome. Due to its cytotoxic effects (Davidson et al., Eur J Cancer 28(2-3):362-8, 1992) and possible role as a mutagen, 5azaC has also been shown to inhibit cell growth and induce apoptosis in certain cancer cells (Pinto et al., Leukemia 7(Suppl 1):51-60, 1993). This drug has been used to induce stable phenotypic alterations in several defined marker systems in mammalian cells (Harris, Cell 29(2):483-92, 1982; Harris, Somat Cell Mol Genet. 10(6):615-24, 1984a; Harris, Somat Cell Mol Genet. 10(3):275-81, 1984b; Harris, Somat Cell Mol Genet. 12(5):459-66, 1986; Holliday, Science 238(4824):163-70, 1987; Jones et al., Cell 20(1):85-93, 1980; Sugiyama et al., Mol Cell Biol 3(11):1937-42, 1983; Taylor et al., Cell 17(4):771-9, 1979).

In our experiments, drug induction with 5azaC indeed led to rapid phenotypic reversion of cholesterol auxotrophy at high frequency. Our results provide a direct link between demethylation of Hsd17b7 and its transcriptional activation in NS0 cells, thereby confirming the role of this gene in relieving nutritional auxotrophy of NS0 cells.

Materials and Methods

Cells and cell culture. NS0 cells were obtained from Pfizer, Inc (Seth et al., Biotech. Bioeng. 90(5):552-67, 2005). They were cultured in CD Hybridoma medium (Invitrogen, Carlsbad, Calif., USA) supplemented with 2 mM L-glutamine (Invitrogen) and 1× Cholesterol lipid Concentrate (Invitrogen). Cholesterol independent cells isolated after 5-azacytidine (5azaC) treatment were cultured in the absence of cholesterol. The cells were maintained in tissue culture flasks in 5% $CO_2$, 37° C. incubator.

Treatment with 5-azacytidine (5azaC) and isolation of cholesterol independent clones. NS0 cells at 200,000 cells/ml were treated with 5azaC (1 μM and 5 μM) in tissue culture flasks. After 48 hrs, the cells were washed and limiting dilution plating was carried out in 10 96-well plates at a dilution of 2,000 cells/well using CD Hybridoma medium without cholesterol supplement. Untreated NS0 cells were also plated in cholesterol-free medium as a control for background cholesterol independent variants in the cell population. The plates were incubated at 5% $CO_2$, 37° C. and saturated humidity for 1-2 weeks.

Genomic DNA isolation and bisulfite modification. Genomic DNA was isolated from NS0 cells using the Wizard® Genomic DNA Purification Kit (Promega, Madison, Wis., USA) according to manufacturer's protocol. The resultant DNA pellet was resuspendend in 100 μl of DNA Rehydration solution provided along with the kit and stored at 4° C. until further processing.

5 μg of genomic DNA was modified using CpGenome™ DNA Modification Kit (Chemicon® International, USA) according to manufacturer's protocol. The CpGenome™ DNA Modification Kit contains reagents required to perform a bisulfite modification on a DNA sample. The bisulfite reaction involves conversion of all unmethylated cytosine bases to uracil, while 5-methylcytosine remains unaltered. Thus, the sequence of DNA after bisulfite modification will depend on the methylation state. The modified DNA was stored as aliquots at −80° C. and subsequently used for methylation specific PCR.

Methylation-specific polymerase chain reaction (MSP). After bisulfite modification, DNA was amplified using methylation-specific PCR (MSP) (Herman et al., Proc Natl Acad Sci USA 93(18):9821-6, 1996). MSP assays for the methylation status of CpG sites by taking advantage of the chemically induced sequence differences resulting from bisulfite modification. Two different primer pairs complementary to the unmethylated (U) and the methylated (M) DNA sequence are used for PCR amplification. The U and M primers for amplifying the CpG island in the upstream 5'-flanking region of Hsd17b7 were designed (U primer—Forward: TAGGATTTTTGTGTTATGTGGTTTT (SEQ ID NO:40), Reverse: CTCTTAACCTAAACCTTAATCCATA (SEQ ID NO:41); M primer-Forward: GATTTTTGTGT-TACGTGGTTTC (SEQ ID NO:42) Reverse CTCTTAAC-CTAAACCTTAATCCGTA (SEQ ID NO:43) using MethPrimer (Li et al., Bioinformatics 18(11):1427-31, 2002). The PCR product sizes for the U and M primers are 191 bp and 188 bp, respectively. PCR amplification was carried out using Platinum® Taq DNA Polymerase (Invitrogen) in a Touchgene® thermal cycler. Cycle conditions included initial denaturation and enzyme activation at 94° C. for 2 min, followed by 40 cycles of 94° C. for 30 sec, 62° C. for 30 sec and 72° C. for 30 sec. Final Extension was carried out at 72° C. for 5 min. PCR products were visualized by electrophoresis through 2% (w/v) agarose gel in 1×TAE buffer and staining with 0.5 μg/ml ethidium bromide.

Reverse Transcription and Real-time comparative quantitative PCR. Total RNA was extracted from cells in exponential growth phase using the RNeasy Mini Kit (Qiagen, Valencia, Calif., USA), followed by reverse transcription with Superscript™ II RNase H⁻ Reverse Transcriptase (Invitrogen). For real-time comparative PCR analysis, samples were prepared using QuantiTect SYBR Green PCR kit (Qiagen) and reactions run on ABI 7700 (Applied Biosystems, Foster City, Calif., USA). Samples were analyzed in duplicates and β-actin was used as the normalization message. The fold change was calculated using the comparative $C_T$ method.

Results

Methylation Status of Hsd17b7 Gene 5'-Flanking Region in NS0 Cells

We have previously observed that the transcript levels of Hsd17b7 in the natural revertant NS0_r was 15 times higher than the wild type NS0 cells and that the suppressed transcription of Hsd17b7 was the cause of cholesterol auxotrophy in NS0 (Seth et al., Biotech. Bioeng. 90(5):552-67, 2005). The natural revertant (NS0_r) was obtained by slow adaptation of wild type NS0 cells to grow in cholesterol-free culture conditions. It is most likely that this slow adaptation of NS0 cells entails a transformation of the entire population or a subpopulation to grow in the new environment; as opposed to a clonal event wherein a single mutated cell, with a growth advantage, overtakes the entire population. A single mutated cell, even with a faster growth rate, is unlikely to be able to overtake the population; furthermore, the frequency is too low for a large number of mutated cells to arise and to replace the original population. Therefore, the adaptation to cholesterol-free growth is unlikely to occur due to the mutation of the Hsd17b7 gene from an inactive form to an active form; rather it is more likely that an active Hsd17b7 already exists in the auxotroph, but the enzyme is expressed only at a low level. The up regulation at the transcript level of Hsd17b7 during the course of adaptation, in a large part of or in the entire cell population, renders it the cholesterol independent growth characteristics. Thus, the up regulation is likely via epigenetic alterations at the DNA level as these may occur in a large population.

Figure 5:
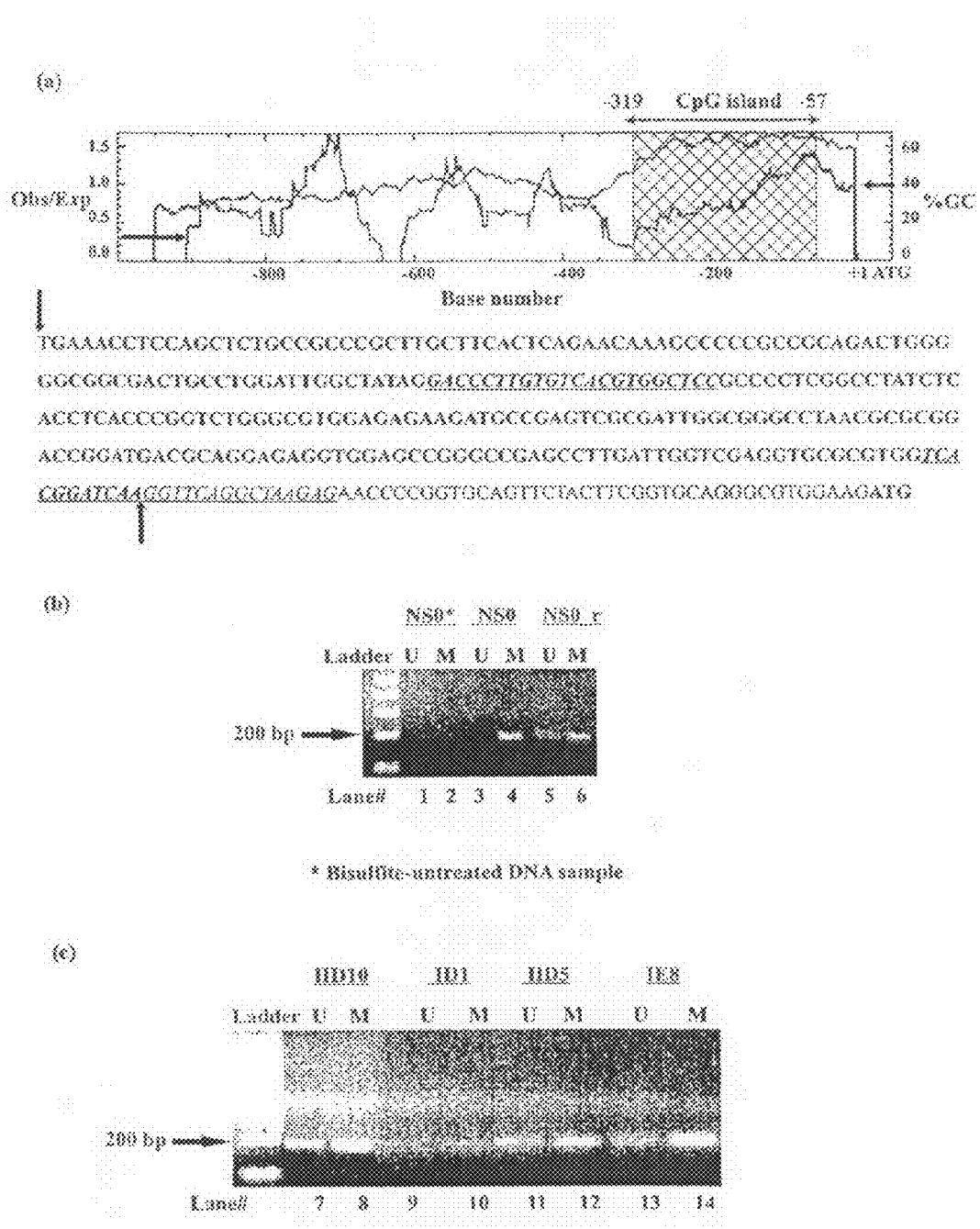
FIG. 5 shows the methylation status of the upstream 5'-region of Hsd17b7 (a) The top panel represents the CpG ratio (observed/expected) and percentage (G+C) content plotted against the position in the analyzed sequence using CpG plot software of EMBOSS— the European Molecular Biology Open Software Suite. The sequence was scanned for the occurrence of CpG in a sliding scale of 100 bp. The count of the number of times CpG occurs in the sequence is the 'observed' number. The 'expected' number of CpGs is calculated based on the frequency of Cs and Gs in the sequence. The CpG island is shown as the hatched area. The lower panel shows the nucleotide sequence upstream of ATG (transcriptional start site) (SEQ ID NO: 1). The CpG island, 319 to 57 bp upstream of ATG is shown in bold letters within block arrows; sequence for the "M" primer pair is italicized and underlined (b) Methylation-Specific PCR analysis of Hsd17b7 in NS0 and NS0_r. Primer sets used for amplification are designated as unmethylated (U) and methylated (M): Lanes 1, 2: amplification of bisulfite-untreated DNA from NS0 cells, Lanes 3, 4 and Lanes 5, 6: amplification of bisulfite-modified DNA from NS0 and NS0_r, respectively; (c) Methylation-Specific PCR analysis of Hsd17b7 in cholesterol independent clones isolated after 5-azacytidine treatment.

We thus explored the possibility that Hsd17b7 in NS0 is epigenetically silenced by DNA methylation. The mouse Hsd17b7 gene is present on chromosome 1. Sequence scan of the upstream 5'-flanking region of Hsd17b7 (nucleotide sequence accession number NT_039185, http://www.ncbi.nlm.nih.gov) using CpGplot (Larsen et al., Genomics 13(4):1095-107, 1992) software of EMBOSS—the European Molecular Biology Open Software Suite (Rice et al., Trends Genet. 16(6):276-7, 2000) revealed a CG-rich region with a CpG island between bases 319 and 57 upstream of the ATG start codon (FIG. 5a, shaded area). This region was designated as the CpG island on the basis of its size being greater than 200 bp, (G+C) content above 50% and an observed versus expected CpG ratio above 0.6 (Gardiner-Garden et al., J Mol Biol 196(2):261-82, 1987).

Methylation-Specific PCR (MSP)

Expression of several genes with CpG-rich regions, or CpG islands, in their promoter region have been reported to be regulated by DNA methylation (Bird, Nature 321(6067):209-13, 1986). The methylation status of the CpG island upstream of Hsd17b7 in NS0 and NS0_r was assessed by performing bisulfite modification on genomic DNA followed by methylation-specific PCR amplification. As described in Materials and Methods, MSP entails a bisulfite modification which converts all the unmethylated cytosine bases in DNA to uracil, while 5-methylcytosine remains unaltered. Therefore, the sequence of DNA after bisulfite modification will be different from the unmodified sequence. MSP was carried out using two sets of primers for the bisulfite modified sequences. One set of primers is specific to the unmethylated (U) sequence and the other specific to the methylated (M) sequence. The results from MSP analysis are shown in FIG. 5b. The DNA sequence from wild type NS0 cells that was not treated with bisulfite did not give rise to any PCR product with the U and M primers as seen in Lanes 1 and 2 of FIG. 5b. After bisulfite modification a strong band was observed on the agarose gel when DNA from wild-type cells was amplified with the M primer specific to the methylated sequence (Lane 4). However, no PCR product was detected when using the U primer (Lane 3); indicating that the Hsd17b7 upstream sequence is methylated in the cholesterol dependent NS0 cells. On the other hand, both methylated and unmethylated alleles of Hsd17b7 exist in the revertant cells NS0_r as seen by strong bands obtained after amplification with both U and M primers (Lanes 5 and 6). The presence of both methylated and unmethylated cytosines in the CpG island region of NS0_r may be attributed to either a heterogeneous population of cells with varying extents of methylation of cytosines or a homogeneous population of cells which have different alleles of methylated and unmethylated sequence.

Reversion Frequency after Treatment with 5-Azacytidine (5azaC)

In order to ascertain the role of DNA demethylation as NS0 cells transition to cholesterol independence, NS0 cells exhibiting very low levels of Hsd17b7 gene expression were used for induced demethylation studies using 5azaC. 5azaC concentrations resulting in 50-70% killing of NS0 were used for this investigation. 5azaC treated cells were aliquoted into 96-well cell culture plates containing cholesterol-free medium. Exposure of NS0 to 5 µM 5azaC resulted in many cholesterol revertants. Survival frequency of nearly 80% of wells in a 96-well plate culture was observed. Spontaneous reversion rate (without 5azaC treatment) and treatment with 1 µM 5azaC was less than $1 \times 10^{-6}$. Previously, cholesterol independent variants of NS0 cells have been isolated by limiting dilution cloning at an average distribution of one cell per well using medium lacking serum and cholesterol (Birch et al., Cytotechnology 15:11-6, 1994). The low reversion frequency ($<10^{-6}$) observed in our experiments suggests that the loss of DNA methylation in cell culture medium is an infrequent event. Also, our observations after 5azaC treatment provided strong indication that methylation mediated gene silencing was responsible for the cholesterol dependence. These results are consistent with those reported in the literature for other systems wherein 5azaC has been shown to produced 10-30% reactivated cells, from a baseline spontaneous reactivation frequency of $10^{-5}$ or less (Holliday et al., Methods 27(2):179-83, 2002). Single cell colonies were isolated from the 96-well culture plates and expanded to tissue culture flasks for further characterization. Cholesterol independent growth of these clones was confirmed by maintaining the surviving clones for more than 20 passages in 24 well plates in cholesterol-free medium.

Figure 6:
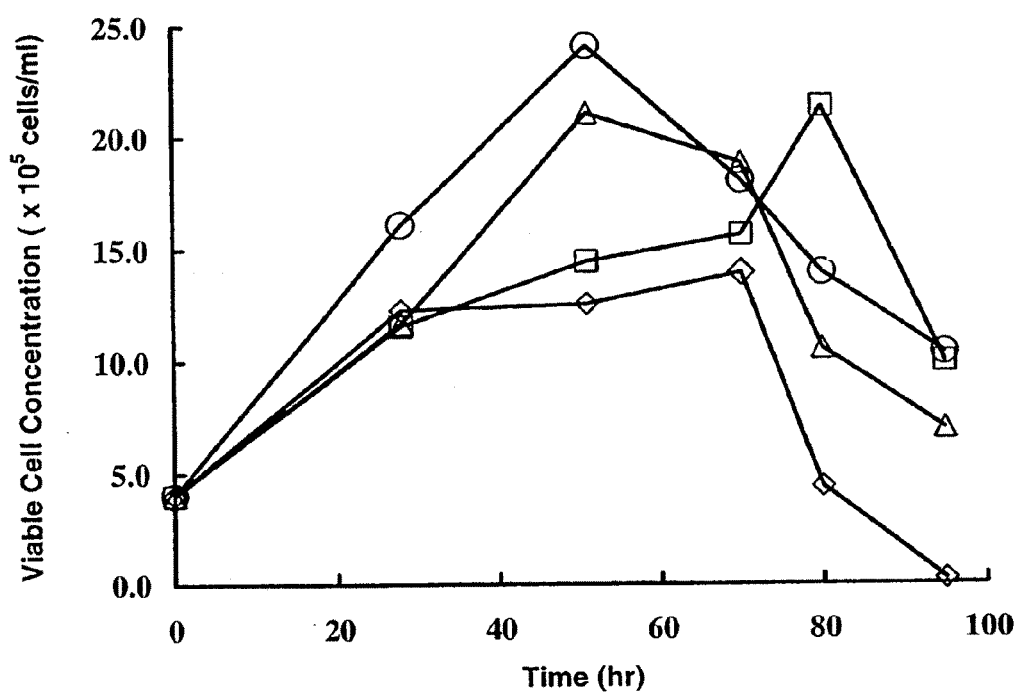
FIG. 6 shows the growth kinetics of NS0 revertants in cholesterol free media after treatment with 5-azacytidine: IE8 (○), IID5 (Δ), ID1 (□), IID10 (◇).

Characterization of Cholesterol-Independent Clones Obtained after 5azaC Treatment Growth kinetics. Twelve cholesterol-independent clones derived from 5azaC treatment were randomly chosen for further studies. The growth rates and the maximal cell density achieved in cholesterol-free medium varied among the clones. Broadly, four clones (IE8, IID5, ID1 and IID10), representative of the range of growth rates exhibited by different clones were further characterized. The growth curves for these clones cultured in the absence of cholesterol are shown in FIG. 6. Amongst the four clones, IE8 had fastest growth rate and achieved peak cell density of about $2.5 \times 10^6$ cells/ml. IID5 grew slower compared to IE8 with maximum cell density of $\sim 2.0 \times 10^6$ cells/ml. ID1 cells exhibited an initial lag phase followed by a rapid rise in the cell density to approximately $2 \times 10^6$ cells/ml. IID10 grew slowest reaching a maximum cell density of only about $1 \times 10^6$ cells/ml followed by a rapid decline in viable cell concentration.

Transcript level of cholesterol biosynthesis genes. The transcript level of six key cholesterol biosynthesis genes—Hmgcr (Hydroxymethylglutaryl-CoA reductase), Sqe (Squalene epoxidase), Lss (Oxidosqualene cyclase), Sc5d (Sterol-C5-desaturase), Ebp (Phenylalkylamine Ca2+ antagonist (amopamil) binding protein) and Hsd17b7, was assessed quantitatively by real-time PCR in the cholesterol independent clones. Among the six genes probed, five, Sqe, Lss, Sc5d, Ebp and Hsd17b7, code for enzymes catalyzing the post-squalene steps of the cholesterol biosynthesis pathway in endoplasmic reticulum. The sixth gene codes for HMGCR, which also exists in the endoplasmic reticulum and is the rate-determining enzyme of the cholesterol biosynthesis pathway (Liscum, DEVaJE, Ed., Biochemistry of Lipids, Lipoproteins and Membranes, 4th Ed.: Elsevier Science B.V., 2002). The transcript expression in these clones isolated after 5azaC treatment was compared to that in NS0 cells (Table 4).

While the transcript level of the other five genes varied somewhat among all clones, that of Hsd17b7 was substantially higher in the revertant clones compared to NS0 cells. IID10 had the highest level of Hsd17b7 expression of about 660 fold of NS0, while IE8 had the lowest at approximately 15 fold. Expression of Hsd17b7 in IID5 and ID1 was in the intermediate range at around 120- and 260-fold respectively.

Expression level of other genes across different clones varied somewhat. IID10, with highest Hsd17b7 expression, also expressed Sc5d and Ebp at level higher than other clones. IE8, while having the lowest extent of up regulation of Hsd17b7, over expressed Sqe by 2.7 fold relative to NS0 (maximum amongst the clones probed). Ebp was up regulated by varying extents in all the probed clones (ID12.0 fold; IE8 1.6 fold; IID5 3.3 fold; IID10 3.6 fold). This trend is opposite to that observed for the natural revertant (Seth et al., J Biotech (in press: published on-line 26 Aug. 2005), where Ebp is down regulated 1.4 fold in the natural revertant (NS0_r) compared to NS0. Since, even low expression level of Ebp does not restrict growth of cells in cholesterol-free medium, up regulation of this gene does not appear to be critical to the cholesterol independent phenotype. For other genes, such as expression of Hmgcr, Lss and Sc5d in IID5, the fold change was too small to indicate any differential expression.

Methylation status of Hsd17b7 in revertant clones. To prove that the high transcript level of Hsd17b7 in the revertant clones was indeed mediated by 5azaC induced demethylation, we probed the methylation status of the CpG island described in the previous section. The results from MSP analysis are shown in FIG. 5c. Both methylated and unmethylated alleles are present in all the cholesterol independent clones obtained after 5azaC treatment (Lanes 7-14). The presence of both methylated and unmethylated cytosines in the CpG island region of these cells is similar to the methylation status of the sequence in NS0_r (described above, FIG. 5b, Lanes 5 and 6). The demethylation of the CpG island is consistent with the activation of Hsd17b7 as the cells are treated with the demethylating drug.

Discussion

Promoter region methylation of cytosine residues has been correlated to transcriptional repression of genes in fungi, plants and animals (Antequera 2003). DNA methylation and its role in the inhibition of transcription can be mediated by two different mechanisms. The methyl moieties directly prevent binding of transcription factors to the DNA sequence and thereby stop transcription. Alternatively, DNA methylation may also operate through complex indirect mechanisms by changing the overall chromatin structure. It has been shown that two of the methylated DNA binding proteins MeCp2 and MDB2 interact with repressor complexes that recruit enzyme histone deacetylase. These deacetylate histones and can lead to an inactive chromatin structure, which results in silencing of the gene (Bird et al., Cell 99(5):451-4, 1999). Establishment of DNA methylation patterns and formation of chromatin which modulates transcription are the two key components of the epigenetically mediated changes in gene expression. More recently, there have been reports suggesting the association of DNA methylation to modifications in chromatin proteins such as histones acetylation and histone methylation (El-Osta et al., Gene Expr 9(1-2):63-75, 2000; Fuks et al., J Biol Chem 278(6):4035-40, 2003; Rountree et al., Oncogene 20(24):3156-65, 2001).

Transformed cells can silence genes by DNA methylation (Holliday et al., Proc Natl Acad Sci USA 95(15):8727-32, 1998). One of the first investigations of gene silencing by DNA methylation in mammalian cells was the study of metallothionein gene in mouse lymphoid cells (Compere et al., Cell 25(1):233-40, 1981). The inhibition of transcription by DNA methylation has been demonstrated by the introduction into cells of genes methylated in vitro (Busslinger et al., Cell 34(1):197-206, 1983; Stein et al., Proc Natl Acad Sci USA 79(11):3418-22, 1982; Vardimon et al., Proc Natl Acad Sci USA 79(4):1073-7, 1982). It was also shown that silent genes could be reactivated by 5azaC (Jones et al., Cell 20(1):85-93, 1980).

TABLE 4

Relative expression of cholesterol biosynthesis genes in isolated clones relative to NS0 cells using quantitative PCR

| Clone | Hmgcr | Sqe | Lss | Sc5d | Ebp | Hsd17b7 |
|---|---|---|---|---|---|---|
| IE8 | (+)2.5 | (+)2.7 | (+)2.0 | 1.3 | (+)1.6 | (+)15 |
| IID5 | 1.0 | 1.2 | 1.1 | 1.1 | (+)3.3 | (+)123 |

TABLE 4-continued

Relative expression of cholesterol biosynthesis genes in isolated clones relative to NS0 cells using quantitative PCR Expression level relative to NS0*

| Clone | Hmgcr | Sqe | Lss | Sc5d | Ebp | Hsd17b7 |
|---|---|---|---|---|---|---|
| ID1 | (+)3.1 | (+)2.3 | (+)1.3 | (+)1.8 | (+)2.0 | (+)260 |
| IID10 | (+)1.8 | 1.2 | (−)1.4 | (+)4.2 | (+)3.6 | (+)670 |
| NS0 | 1.0 | 1.0 | 1.0 | 1.0 | 1.0 | 1.0 |

*(+) Up-regulation in isolated clone, ratio is Isolated Clone/NS0
(−) Down-regulation in isolated clone, ratio is NS0/Isolated Clones
Hmgcr (Hydroxymethylglutaryl-CoA reductase); Sqe (Squalene epoxidase); Lss (Oxidosqualene cyclase); Sc5d (Sterol-C5-desaturase), Ebp (Phenylalkylamine Ca2+ antagonist (amopamil) binding protein)

Upon 5azaC treatment, the resulting de-silenced clones exhibited markedly different transcript levels (Table 4). It has been reported that the extent of gene de-silencing and hence activation depends on both the degree of DNA de-methylation and the cell selection conditions (Holliday et al., Russo et al., Eds., Epigenetic mechanisms of gene regulation: Cold Spring Harbor Laboratory Press, 1996). The different transcript levels are thus likely to be due to difference in methylation status of distinct CpG sites among different clones. Loss of several methylcytosines in contrast to replacement of a single one is essential for reversal of a specific phenotype. Also, after gene activation, silencing may be re-imposed if the gene is dispensable and the cells have a growth advantage without its transcription and translation. In this experiment, drug induction with 5azaC was followed by limiting dilution cloning and growth in cholesterol-free medium, thereby maintaining the selection pressure which led to activation of Hsd17b7. Subsequent possible silencing of Hsd17b7 after removal of selection pressure and maintenance for a few cell doublings was not investigated.

We noted that the two isolated clones, IE8 and IID5 obtained after 5azaC treatment, appear to have similar, high growth rates but exhibit widely different transcript levels of Hsd17b7. Hsd17b7 transcript expression is around 15 fold higher in IE8, in contrast to approximately 120 fold up regulation in IID5, relative to the transcript level in the wild type. We have previously observed that NS0_r, obtained after complete adaptation to cholesterol-free medium, has elevated Hsd17b7 levels of around 15 fold relative to NS0. Taken together, it is likely that gene activation leading to around 10 times over expression of Hsd17b7 transcript compared to the wild type is sufficient to alleviate cholesterol auxotrophy.

Here we demonstrate that epigenetic modification of Hsd17b7 occurred as NS0 cells transitioned from cholesterol-requiring to cholesterol-free culture conditions. Methylation of the 5' upstream sequence of Hsd17b7 in the wild type cells, revealed by Methylation Specific PCR analysis (MSP), correlated well with the lack of expression of this gene as seen from the real-time PCR analysis. Additionally, increased expression of the endogenous gene in the revertant cells correlated with the presence of unmethylated DNA in the NS0_r cell population. Although multiple factors may lead to silencing of Hsd17b7 in wild type cells, from our observations, we conclude that DNA methylation is responsible at least in part for the cholesterol auxotrophy. Whether the exact mechanism underlying the methylation mediated gene silencing of Hsd17b7 is the lack of binding of transcription factors to the methylated DNA or due to structural condensation of the methylated sequence remains to be determined. Furthermore, we present modification of the epigenetic patterns inside the cell as an alternative way of attaining a favorable phenotype, compared to genetic manipulation of the cell via expression of an exogenous gene.

Cholesterol is an essential component of the lipid bilayer membranes that affect many physiological functions. Normally cholesterol is delivered to cultured cells by complexing with cyclodextrin or bovine serum albumin; the former requires special formulation while the latter introduces animal component product which is nowadays highly undesirable for biomanufacturing. The reversal of cholesterol auxotrophy eliminates that undesired practice in growing NS0 cells.

In this example, we focused on the adaptation of NS0 cells to cholesterol independence. The results obtained lead us to speculate the role of gene silencing or de-silencing in many other commonly practiced adaptation processes that confer traits desirable in bioprocessing. Cell line development is probably the most important component in establishing an efficient cell culture bioprocess. The development and establishment of a high producing cell line and the process for each new potential biologic involves a series of extensive adaptation procedures. These adaptation procedures typically involve passaging cells over long periods of time, gradually transferring the cells to a new chemical environment via media manipulation and/or a new physical environment by altering the growth surface. These processes, although fairly well-established have largely remained empirical. Few detailed studies have been performed to compare the physiological and genotypical changes that have incurred in the cells during the course of adaptation. An insight into the molecular changes underlying various adaptation processes, either at the host cell or at the post-clonal selection level will undoubtedly facilitate cell line development.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A selectable NS0 cell comprising an expression cassette comprising (a) a first nucleotide sequence encoding a polypeptide or polynucleotide of interest, and (b) a second nucleotide sequence encoding Hsd17b7, wherein the first and second nucleotide sequences are linked such that production of Hsd17b7 protein is indicative of production of the polypeptide or polynucleotide of interest.

2. A selectable NS0 cell comprising an expression cassette comprising (a) a first nucleotide sequence encoding a polypeptide or polynucleotide of interest, and (b) a second nucleotide sequence encoding a truncated SREBP protein, wherein the first and second nucleotide sequences are linked such that production of a truncated SREBP protein is indicative of production of the polypeptide or polynucleotide of interest.

* * * * *